(12) United States Patent
Kuhn

(10) Patent No.: US 12,070,226 B2
(45) Date of Patent: Aug. 27, 2024

(54) MEDICAL DEVICE FOR TISSUE HEMOSTASIS OR CLOSURE

(71) Applicant: MICRO-TECH (NANJING) CO., LTD., Jiangsu (CN)

(72) Inventor: Daniel Kuhn, Düsseldorf (DE)

(73) Assignee: MICRO-TECH (NANJING) CO., LTD., Jiangsu (CN)

( * ) Notice: Subject to any disclaimer, the term of this patent is extended or adjusted under 35 U.S.C. 154(b) by 538 days.

(21) Appl. No.: 17/598,045

(22) PCT Filed: Apr. 13, 2020

(86) PCT No.: PCT/CN2020/084497
§ 371 (c)(1),
(2) Date: Sep. 24, 2021

(87) PCT Pub. No.: WO2020/211725
PCT Pub. Date: Oct. 22, 2020

(65) Prior Publication Data
US 2022/0160366 A1    May 26, 2022

(30) Foreign Application Priority Data
Apr. 17, 2019 (EP) .................................. 19169940

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/29* (2013.01);
(Continued)

(58) Field of Classification Search
CPC . A61B 17/122; A61B 17/128; A61B 17/1285; A61B 17/29; A61B 2017/0034;
(Continued)

(56) References Cited

U.S. PATENT DOCUMENTS 7,094,245 B2 * 8/2006 Adams .................... A61B 90/03
606/139
7,879,052 B2 * 2/2011 Adams ................. A61B 17/122
606/157
(Continued)

FOREIGN PATENT DOCUMENTS

CN 102626335 A 8/2012
CN 102090910 B 12/2012
(Continued)

OTHER PUBLICATIONS

European Search Report and Opinion with regard to EP19185556.8 completed Jan. 7, 2020.
(Continued)

*Primary Examiner* — Ryan J. Severson
(74) *Attorney, Agent, or Firm* — BCF LLP

(57) ABSTRACT

A medical device for tissue hemostasis or closure that is used by means of an endoscope, the medical device comprising: a handle (1); a sheath apparatus (2) attached to the handle (1); a clamping apparatus (3) comprising a clamping base (6) and at least or exactly two clamping arms (7a, 7b), the clamping base (6) specifically being a sleeve and being disposed on a distal end of the sheath apparatus (2); a control wire (4) that extends to pass through the sheath apparatus (2) and that can move reversibly in a distal direction and a proximal direction; and an actuator (5), the actuator (5) being coupled to a proximal end of the control wire (4) and
(Continued)

being capable of actuating such that the control wire (4) moves reversibly in the distal direction and the proximal direction.

18 Claims, 20 Drawing Sheets

(51) Int. Cl.
  *A61B 17/29* (2006.01)
  *A61B 17/00* (2006.01)
  *A61B 17/12* (2006.01)
(52) U.S. Cl.
  CPC ............ *A61B 2017/0034* (2013.01); *A61B 2017/00473* (2013.01); *A61B 2017/12004* (2013.01); *A61B 2017/2931* (2013.01); *A61B 2017/2934* (2013.01); *A61B 2017/2936* (2013.01); *A61B 2017/2946* (2013.01); *A61B 2017/2947* (2013.01)
(58) Field of Classification Search
  CPC ........... A61B 2017/00477; A61B 2017/00862; A61B 2017/12004; A61B 2017/2936
  See application file for complete search history.

(56) References Cited

U.S. PATENT DOCUMENTS

| | | | | |
|---|---|---|---|---|
| 8,062,311 | B2 * | 11/2011 | Litscher | A61B 17/122 606/143 |
| 8,070,760 | B2 * | 12/2011 | Fujita | A61B 17/1227 606/151 |
| 8,858,588 | B2 * | 10/2014 | Sigmon, Jr. | A61B 17/08 606/205 |
| 8,915,837 | B2 * | 12/2014 | Wells | A61B 17/122 606/139 |
| 9,084,604 | B2 * | 7/2015 | Litscher | A61B 17/122 |
| 9,510,836 | B2 * | 12/2016 | Zhu | A61B 17/122 |
| 9,795,390 | B2 * | 10/2017 | Jin | A61B 17/1285 |
| 10,172,623 | B2 * | 1/2019 | Adams | A61B 17/1285 |
| 10,470,777 | B2 * | 11/2019 | Litscher | A61B 17/1285 |
| 10,799,358 | B2 * | 10/2020 | Erickson | A61B 17/295 |
| 10,820,904 | B2 * | 11/2020 | Ryan | A61B 17/1285 |
| 11,020,125 | B2 * | 6/2021 | Randhawa | A61B 17/122 |
| 11,045,194 | B2 * | 6/2021 | King | A61B 17/128 |
| 11,160,558 | B2 * | 11/2021 | Lehtinen | A61B 17/10 |
| 11,857,213 | B2 * | 1/2024 | Nelson | A61B 17/282 |
| 2003/0069592 | A1 | 4/2003 | Adams et al. | |
| 2005/0107809 | A1 * | 5/2005 | Litscher | A61B 17/1285 606/142 |
| 2005/0182426 | A1 * | 8/2005 | Adams | A61B 17/083 606/213 |
| 2009/0105533 | A1 | 4/2009 | Fujita | |
| 2012/0065647 | A1 * | 3/2012 | Litscher | A61B 17/1285 606/143 |
| 2012/0071898 | A1 | 3/2012 | Wells et al. | |
| 2012/0089176 | A1 * | 4/2012 | Sigmon, Jr. | A61B 17/10 606/205 |
| 2014/0088616 | A1 | 3/2014 | Clerc et al. | |
| 2014/0171973 | A1 | 6/2014 | Zhu | |
| 2015/0282813 | A1 | 10/2015 | Litscher et al. | |
| 2016/0128698 | A1 * | 5/2016 | Adams | A61B 17/083 606/142 |
| 2016/0367258 | A1 * | 12/2016 | Jin | A61B 17/1285 |
| 2018/0049745 | A1 | 2/2018 | Randhawa et al. | |
| 2018/0078262 | A1 | 3/2018 | Lehtinen et al. | |
| 2018/0085122 | A1 | 3/2018 | Ryan et al. | |
| 2018/0153552 | A1 | 6/2018 | King et al. | |
| 2019/0053904 | A1 | 2/2019 | Erickson et al. | |
| 2019/0090883 | A1 * | 3/2019 | Adams | A61B 17/1227 |
| 2022/0160366 | A1 * | 5/2022 | Kuhn | A61B 17/122 |
| 2022/0167990 | A1 * | 6/2022 | Kuhn | A61B 17/122 |
| 2022/0202422 | A1 * | 6/2022 | Kuhn | A61B 17/122 |

FOREIGN PATENT DOCUMENTS

| | | |
|---|---|---|
| CN | 202699217 U | 1/2013 |
| CN | 202699218 U | 1/2013 |
| CN | 103200883 A | 7/2013 |
| CN | 102626335 B | 4/2014 |
| CN | 103989500 A | 8/2014 |
| CN | 203828993 U | 9/2014 |
| CN | 105935304 A | 9/2016 |
| CN | 206239447 U | 6/2017 |
| CN | 107115130 A | 9/2017 |
| CN | 206482631 U | 9/2017 |
| CN | 107684448 A | 2/2018 |
| CN | 108635007 A | 10/2018 |
| CN | 109009310 A | 12/2018 |
| CN | 109199515 A | 1/2019 |
| CN | 208435704 U | 1/2019 |
| CN | 109480950 A | 3/2019 |
| CN | 109805977 A | 5/2019 |
| CN | 209884245 U | 1/2020 |
| EP | 1328199 A1 | 7/2003 |
| EP | 1829489 A1 | 9/2007 |
| EP | 2371303 A1 | 10/2011 |
| EP | 2380509 A2 | 10/2011 |
| EP | 3053532 A1 | 8/2016 |
| EP | 3081174 A1 | 10/2016 |
| EP | 1328199 B1 | 6/2018 |
| WO | 95/11620 A2 | 5/1995 |
| WO | 2008/070486 A2 | 6/2008 |
| WO | 2011/022246 A1 | 2/2011 |
| WO | 2012/051191 A2 | 4/2012 |
| WO | 2018235402 A1 | 12/2018 |

OTHER PUBLICATIONS

English Abstract for CN103200883 retrieved on Espacenet on Jul. 13, 2021.
European Search Report and Opinion with regard to EP19169946.1 completed Oct. 15, 2019.
Insternational Search Report (including Translation) and Writte Opinion with regard to PCT/CN2020/085337 completed Jun. 23, 2020.
International Search Report (including English Translation) and Written Opinion with regard to PCT/CN2020/084280 mailed Jun. 23, 2020.
English Abstract for CN108635007 retrieved on Espacenet on Sep. 20, 2021.
English Abstract for CN206239447 retrieved on Espacenet on Sep. 27, 2021.
English Abstract for CN109199515 retrieved on Espacenet on Sep. 27, 2021.
English Abstract for CN206482631 retrieved on Espacenet on Sep. 27, 2021.
English Abstract for CN102626335 retrieved on Espacenet on Jul. 13, 2021.
English Abstract for CN202699217 retrieved on Espacenet on Sep. 27, 2021.
English Abstract for CN202699218 retrieved on Espacenet on Sep. 27, 2021.
English Abstract for CN208435704 retrieved on Espacenet on Jul. 13, 2021.
International Search Report (including English Translation) and Written Opinion with regard to PCT/CN2020/084497 mailed Jun. 29, 2020.
English Abstract for CN109805977 retrieved on Espacenet on Jul. 13, 2021.
English Abstract for CN209884245 retrieved on Espacenet on Jul. 13, 2021.
English Abstract for CN103989500 retrieved on Espacenet on Jul. 13, 2021.
English Abstract for CN203828993 retrieved on Espacenet on Jul. 13, 2021.
English Abstract for CN109009310 retrieved on Espacenet on Jul. 13, 2021.

(56) References Cited

OTHER PUBLICATIONS

English Abstract for CN105935304 retrieved on Espacenet on Jul. 13, 2021.
English Abstract for CN109480950 retrieved on Espacenet on Jul. 13, 2021.
English Abstract for CN107115130 retrieved on Espacenet on Jul. 13, 2021.
English Abstract for CN107684448 retrieved on Espacenet on Sep. 22, 2021.
European Search Report and Opinion with regard to the EP19169940.4 completed Dec. 3, 2019.
Partial European Search Report with regard to the EP19169940.4 completed Oct. 8, 2019.
English Abstract for CN102090910 retrieved on Espacenet on Sep. 22, 2021.

* cited by examiner

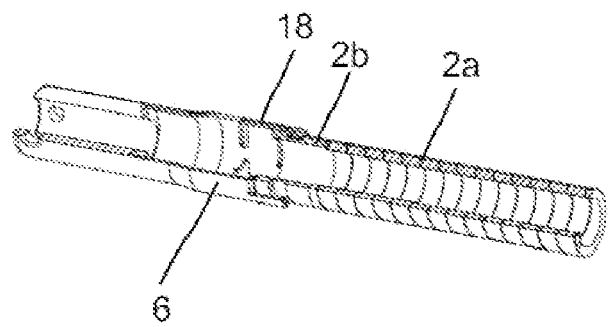
FIG. 35
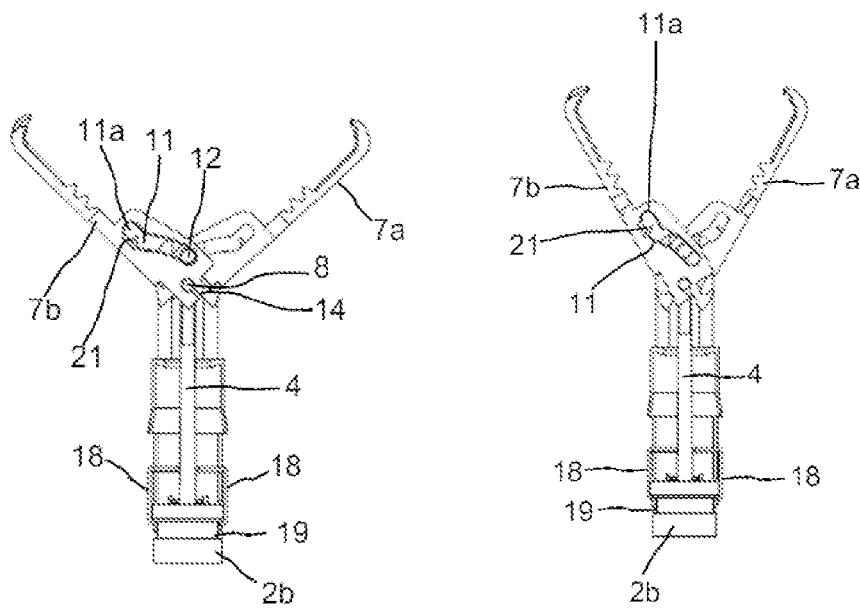
FIG. 36     FIG. 37
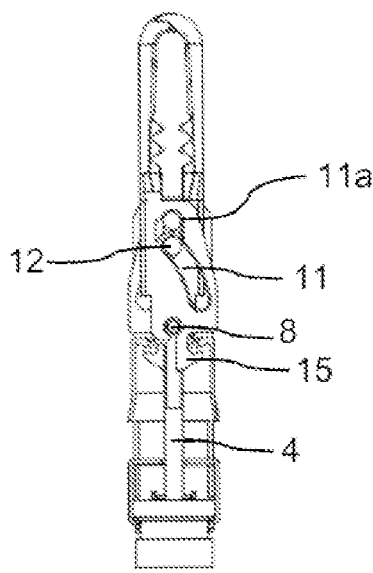 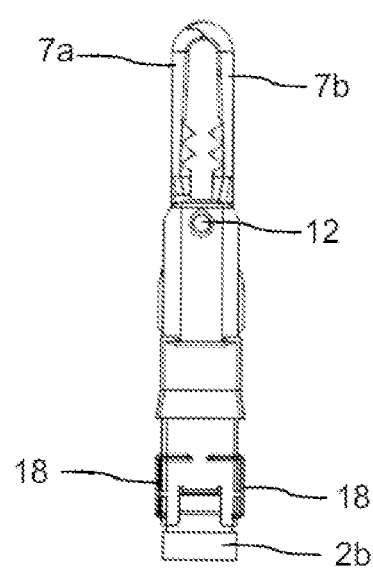
FIG. 38     FIG. 39

MEDICAL DEVICE FOR TISSUE HEMOSTASIS OR CLOSURE

CROSS-REFERENCE TO RELATED APPLICATION

The present disclosure claims the priority to the European patent application with the filing number EP19169940.4 filed on Apr. 17, 2019 with the European Patent Office, and entitled "Medical Device for Causing the Hemostasis of a Blood Vessel", the contents of which are incorporated herein by reference in entirety.

TECHNICAL FIELD

The present disclosure relates to the technical field of medical devices, in particular to a medical device for tissue hemostasis or closure for use through an endoscope.

BACKGROUND ART

Medical devices of this kind are known in the prior art, for example from EP 1 328 199 B1, and in particular used to treat gastrointestinal bleedings. Specifically, such devices are used to set clamps or clips to pinch a bleeding vessel applying sufficient constrictive force to the blood vessel so as to limit or interrupt blood flow passing therethrough.

The medical device known from EP 1 328 199 B1 includes a handle and a sheath, which is attached to the handle. A control wire extends through the sheath and can be actuated by an actuator, which is coupled to a proximal end of the control wire so as to reversibly move the control wire in distal and proximal directions. The medical device further includes a clamp device including a sleeve provided on a distal end of the sheath and a clip with two clamp arms, and the clamp arms are coupled to a distal end of the control wire by means of a J-hook. The clamp arms cooperate with the sleeve in such a way, that the clamp arms engage a front edge of the sleeve to be elastically deformed inwardly, thus being closed, when the control wire is pulled in a proximal direction, whereas the clamp arms are distally pushed out of the sleeve and automatically reopen due to their elastic restoring force, when the control wire is pushed in the distal direction. Since the clamp device can be repeatedly opened and closed, setting of the clamp device is possible in an easy way.

Once the clamp device is positioned correctly, the clamp device with the clamp arms and the sleeve can be disconnected from the rest of the medical device. In order to do so the control wire is further pulled back, when the clamp device is completely closed, so that the J-hooks break and thus the connection between the clamp arms and the control wire is interrupted. Moreover, by further pulling back the control wire, a retainer which connects the control wire with the sleeve is actuated, in order to disconnect the retainer from the sleeve and thus the control wire from the sleeve.

SUMMARY

In order to solve at least one problem in the prior art, objectives of the present disclosure include, for example, providing a medical device of the above mentioned kind that is easy to operate as well as easy to manufacture and assemble. According to the present disclosure, at least one objective in the prior art may be achieved by the medical device of the following kind.

The present disclosure relates to a medical device for tissue hemostasis or closure for use through an endoscope, the medical device including:
  a handle;
  a sheath device, which is attached to the handle;
  a clamp device, including a clamp base in particular in the form of a sleeve provided on a distal end of the sheath device and at least two or exactly two clamp arms;
  a control wire, extending through the sheath device and reversibly movable in distal and proximal directions; and
  an actuator, coupled to a proximal end of the control wire and operable to reversibly move the control wire in the distal and proximal directions,
  wherein the clamp arms are each coupled to the distal end of the control wire and wherein the clamp device is operable to open and close the clamp arms by a movement of the control wire such that a movement of the control wire in the proximal direction is translated into a closing movement of the clamp arms and the movement of the control wire in the distal direction is translated to an opening movement of the clamp arms.

In the medical device, the clamp arms are coupled to the control wire by means of a pivot pin which is provided at a distal end section of the control wire and extends through corresponding through-holes provided in tail ends of the clamp arms, and that exit-passages are provided in the tail ends of the clamp arms at the proximal side of the through-holes, through which after closing the clamp arms the pivot pin can be pulled out of the through-holes and from the clamp arms spreading apart the tail end sections of the clamp arms on opposite sides of the exit-passages without breaking them by a proximal movement of the control wire in order to uncouple the control wire from the clamp arms.

According to the present disclosure the clamp arms are directly coupled to the control wire, thus omitting the necessity to provide for a separate connecting element for example in the form of a J-hook. Specifically the control wire is provided at its distal end section with a pivot pin, which engages corresponding through-holes provided in proximal end sections of the clamp arms.

The through-holes are open to the proximal end of the clamp arms. Specifically exit-passages are provided which are designed such, that they are small enough, so that the pivot pin cannot fall out of the clamp arms unintentionally, but can be intentionally pulled out of the through-holes through the exit-passages by exerting a sufficiently high tensile force to the control wire, so that the tail end sections of the clamp arms on the opposite side of the exit-passages are spread apart and thus deformed.

The exit-passages may for example be formed by slits in the tail ends of the clamp arms.

According to a further embodiment of the disclosure the tail end sections of the clamp arms are elastically or plastically deformed, when they are spread apart. In any way the arrangement is such that the tail end sections do not break in order to avoid, that parts of the breakable arms remain freely in the body of a patient.

According to another embodiment of the present disclosure, the tail end sections of the clamp arms on the opposite sides of the exit-passages engage behind at least one shoulder of the clamp base in order to lock the clamp arms to the clamp base. Optionally, the tail end sections of the clamp arms on the opposite sides of the exit-passages form hooks that engage behind the at least one shoulder of the clamp base in order to lock the clamp arms to the clamp base.

The shoulder can be formed by an annular projection of the clamp base, wherein the annular projection in particular forms a distal end face of the clamp base with a central opening, through which the tail end sections of the clamp arms extend into the clamp base when the clamp arms are fully closed.

If the tail end sections on the opposite side of the exit-passages of the clamp arms are plastically deformed, when the pivot pin is pulled out of engagement from the clamp arms provision is made, that their proximal ends are positioned behind, i.e. on the proximal side of the shoulder of the clamp base, so that they are plastically deformed to engage behind the shoulder, to lock the clamp arms to the clamp base, and consequently the clamp arms cannot be removed from the clamp base anymore. In this way further separate locking elements are not necessary.

According to a further embodiment of the present disclosure a coupling head is provided at the distal end of the control wire and the pivot pin is provided on the coupling head. The pivot pin may have two pivot pin sections extending from opposite side of the coupling head into the through-holes of the clamp arms which are positioned on opposite sides of the coupling head. This arrangement is useful, when the clamp arms are provided on different sides of the coupling head. Alternatively the coupling head may include a U-shaped holding structure opened to its distal side, wherein the clamp arms are partly arranged between legs of the U-shaped holding structure and the pivot pin is held between the legs of the U-shaped holding structure and extends through the through-holes of the clamp arms, and wherein, in particular, the clamp arms extend laterally outwards of an open lateral side of the U-shaped holding structure. In this embodiment the clamp arms are arranged in the U-shaped holding structure and may therefore be in direct contact with each other.

According to a further aspect of the present disclosure the objective is solved by a medical device of the initially mentioned kind, which is characterized in that the clamp device includes exactly two clamp arms which are provided as separate elements, that are each coupled to the distal end of the control wire in a pivotal manner around a common pivot axis defined by a pivot pin, wherein each clamp arm is provided with a guide groove and the guide grooves of the clamp arms partially overlap each other; and a guide pin which is attached to the clamp base and extends through the guide grooves in the overlapping parts thereof, so that by the engagement of the guide pin and the guide grooves a movement of the control wire in the proximal direction is translated into a closing movement of the clamp arms, and a movement of the control wire in the distal direction is translated into an opening movement of the clamp arms around the pivot axis.

According to this embodiment the clamp arms are separate elements/components that are not directly connected to one another. Instead they are each coupled to the control wire by the engagement of their through-holes with the pivot pin. Moreover they are coupled by the engagement of the guide pin and the guide grooves to the clamp base in such a way, that an axial movement of the control wire is translated into closing/opening movements of the clamp arms around the pivot axis. According to another embodiment of the present disclosure the guide pin is held between two bearing arms, extending in the distal direction from the clamp base, in particular at the free end sections of the bearing arms. The clamp base and the bearing arms form a clamp housing.

According to another embodiment of the present disclosure, holding noses are provided on the clamp arms, the holding noses extending into the guide grooves from a lateral side thereof and being designed in such a way, that they allow the guide pins to pass them to reach the distal ends of the guide grooves but prevent passing of the guide pins in the opposite direction, wherein in particular the guide grooves have a straight, axially extending distal end section, in which the guide pins can move without incurring rotation of the clamp arms and the holding noses extend into the straight distal end sections. In particular recesses may be formed in the lateral sides of the guide grooves on a distal side of the holding nose, into which the holding noses are elastically deformed to allow the guide pins to pass the holding noses and reach their distal end positions in the guide grooves.

According to this embodiment the guide pin is captured in the distal ends of the guide grooves by means of the holding noses, thus locking the clamp to the clamp base. In this way further locking elements are no more necessary.

A further embodiment of the present disclosure can be formed such that the clamp base is reversibly and directly connected to the sheath device by at least one connecting element and that a release arrangement cooperating with each connecting element is provided and can be actuated by movement of the control wire in the proximal direction to release the clamp base from the sheath device, when the clamp arms have been closed, wherein each connecting element is fixedly attached to the clamp base or part of the clamp base and releasably connected to the sheath device, or wherein each connecting element is fixedly attached to or part of the sheath device and releasably connected to the clamp base.

According to this embodiment the clamp base and the sheath device are directly connected to each other by corresponding connecting elements, which are fixedly provided on the one component and releasably connected to the other component. In this way a very reliable and stable connection between the clamp base and the sheath device is obtained, without necessitating any separate connecting elements. In this way the medical device according to the present disclosure is simple in design and easy to manufacture. The connecting elements can be actuated in order to release the clamp base from the sheath device, when the clamp arms have been closed. Specifically the arrangement is such that when the clamp arms have been closed and the control wire is moved further in the proximal direction the clamp base is released from the sheath device.

According to an embodiment of the present disclosure the sheath device includes a sheath and a connect tube fixedly provided on the distal end of the sheath. For example the connect tube can be welded to the sheath. Optionally the sheath can be an extendable coiled sheath.

Optionally not a single, but several connecting elements are provided with a regular angular offset along an outer circumference of the clamp base. In particular two connecting elements are provided on opposite sides of the clamp base.

According to a further embodiment of the present disclosure each connecting element is fixedly attached to or part of the clamp base and releasably connected to the sheath device, in particular the connect tube of the sheath device, and has a free end formed as an engagement portion, which engages corresponding engagement means of the sheath device, in particular a recess and preferably a ring groove provided in an outer circumferential surface of the sheath device, in order to releasably connect the clamp base to the sheath device. If the recess is formed as a ring groove the clamp base can be turned by 360° relative to the sheath device.

A further embodiment of the present disclosure provides, that the release arrangement comprises a protrusion provided on the control wire and arranged to come into engagement with each connecting element by a proximal movement of the control wire to release the clamp base from the sheath device, when the clamp arms have been closed, wherein the protrusion in particular is formed as part of a coupling head provided at the distal end of the control wire.

According to a further embodiment of the present disclosure the connecting elements are elastically or plastically deformed by the engagement with the protrusion in order to bring the connecting portion of each connecting element out of engagement of the corresponding engagement means of the sheath device. In this case, optionally, each connecting element is provided in the form of a connecting arm that has an inwardly bulged section, the protrusion engaging the inwardly bulged section in order to elastically or plastically deform the connecting arm outwardly.

In this embodiment the protrusion provided on the control wire engages the inwardly sections in order to elastically deform the connecting arms outwardly, so that their free ends, which engage the corresponding engagement means of the sheath device, are also deformed outwardly and come out of engagement of the engagement means.

According to a further embodiment of the present disclosure each connecting element is plastically deformed by the engagement with the protrusion in order to bring its connecting portion out of engagement from the corresponding engagement means of the sheath device. Optionally each connecting element is formed as a C-shaped connecting element, wherein a central bar of the C-shaped connecting element is attached at a connection site to the clamp base, a distal C-leg extends inwardly into the clamp base, so that it can be engaged by the protrusion, and the other proximal C-leg forms the engagement portion and extends inwardly to engage the corresponding engagement means of the sheath device and wherein by the engagement of the protrusion with the distal C-leg the connecting element is pivoted around the connection site to move the proximal C-leg out of engagement from the sheath device.

Both embodiments allow a simple construction/design of the clamp base, thus keeping the manufacturing costs low.

When the connecting element is fixedly attached to the sheath device, in particular a connect tube of the sheath device, or part thereof and releasably connected to the clamp base, a further embodiment of the present disclosure provides, that each connecting element is provided in the form of resilient, elastically deformable connecting arm, wherein the proximal end of the connecting element is attached to or part of the sheath device and the free distal end of the connecting element forms the engagement portion to be brought into engagement with corresponding engagement means of the clamp base, in particular a recess and preferably a ring groove provided in the outer circumferential surface of the clamp base, and wherein each connecting element has an inwardly bulged section and the release arrangement includes a protrusion, in particular a cylindrical protrusion provided on the control wire and cooperating with the inwardly bulged sections in such a way, that the protrusion presses the inwardly bulged section outwardly in order to elastically deform the connecting elements, so that the engagement portions of the connecting elements are pressed inwardly into engagement with the corresponding engagement means of the clamp base when the protrusion is located between the inwardly bulged sections, and that when the control wire in the closed state of the clamp arms is moved further in the proximal direction the protrusion comes out of engagement from the inwardly bulged sections, so that the inwardly bulged sections are deformed inwardly by their elastic restoring force and the connecting portions come out of engagement of the corresponding engagement means of the clamp base.

In this embodiment the elastic connecting arms forming the connecting elements are actively held in engagement with the recess/groove provided in the clamp base by the engagement of the protrusion and the inwardly bulged sections of the connecting arms. Once this engagement is no more existent, because the control wire is pulled back in the proximal direction so far, that the protrusion is no more between the bulged sections, the later are elastically deformed inwardly by their restoring force. In other words the connection between the sheath device and the clamp base is passively released by moving the protrusion of the control wire out of the range of the bulged sections.

Optionally, on the distal side of the bulged sections a connecting element extends out of the connect tube through windows provided in a circumferential wall of the connect tube, and when the protrusion is located between the inwardly bulged sections so that the connecting elements are outwardly deformed, the connecting elements are pressed against abutment faces, in particular slanted abutment faces, on the proximal side of the windows leading to an inward deformation of the distal ends of the connecting elements so that their connecting portions are pressed against the corresponding engagement means of the clamp base.

BRIEF DESCRIPTION OF DRAWINGS

Embodiments of the present disclosure will be described in the following with reference to the accompanying drawings. In these drawings, FIG. 35 is a sectioned view of the arrangement of FIG. 34, FIG. 36 is a partially sectioned view of the clamp device with the clamp arms in fully open state, FIG. 37 is a partially sectioned view of the clamp device with partially closed clamp arms, FIG. 38 is a partially sectioned view of the clamp device with closed clamp arms, FIG. 39 corresponds to FIG. 38 without sections, FIG. 40 corresponds to FIG. 38 and shows the arrangement from a different angle, FIG. 41 corresponds to FIG. 40 and shows the arrangement with further retracted control wire, FIG. 42 corresponds to FIG. 41 with the clamp base in sectional view and the clamp arms in fully closed and secured position.

Figure 1:
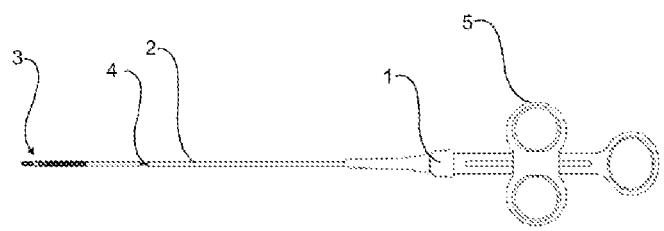
FIG. 1 shows a front view of a medical device according to an embodiment of the present disclosure.

Reference signs: 1—handle; 2—sheath device; 2a—sheath; 2b—connect tube; 3—clamp device; 4—control wire; 5—actuator; 6 clamp base; 7a, 7b—clamp arm; 8—pivot pin; 8a, 8b—pivot pin section; 9—through-hole; 10—coupling head; 11—guide groove; 11a—straight distal end section; 11b—recess, 12—guide pin; 13a, 13b—bearing arm; 14—exit-passage; 15, 16—tail end section; 17—shoulder; 18—connecting element; 18a—bulged section; 19—groove; 20—protrusion; 21—holding nose; 22—web; 23—window; 24—abutment face.

DETAILED DESCRIPTION OF EMBODIMENTS

In FIG. 1 to FIG. 26 an embodiment of a medical device according to the present disclosure is shown. The medical device is used to set clamps for causing hemostasis of blood vessels located along the gastrointestinal tract, wherein the clamps are delivered to a target site through an endoscope.

The medical device includes a handle 1, a sheath device 2 attached to the handle 1, and a clamp device 3 provided on a distal end of the sheath device 2. A control wire 4 extends through the sheath device 2 and is at its proximal end connected to an actuator 5, which is slidingly held on the handle 1 and can be actuated to reversibly move the control wire 4 in distal and proximal directions.

The clamp device 3 includes a clamp base 6 formed as a sleeve and two clamp arms 7a, 7b, which are each coupled to the distal end of the control wire 4. Specifically the two clamp arms 7a, 7b are separate elements/components that are coupled to the control wire 4 by means of a pivot pin 8, which is provided at a distal end section of the control wire 4 and extends through corresponding through-holes 9 provided in proximal end sections of the clamp arms 7a, 7b. In the present embodiment the pivot pin 8 is provided on a coupling head 10, which is provided at the distal end of the control wire 4.

The coupling head 10 has a U-shaped or bifurcated holding structure which is open on its distal end, and the clamp arms 7a, 7b are partly arranged between the legs of the U-shaped holding structure of the U-shaped holding structure. The pivot pin 8 is held between the legs of the U-shaped holding structure and extends through the through-holes 9 of the clamp arms 7a, 7b, which in turn extend laterally outwards of an open lateral side of the U-shaped holding structure.

The two clamp arms 7a, 7b are coupled to the distal end of the control wire 4 so that they can be rotated around a common pivot axis formed by the pivot pin 8 in order to open and close the clamp arms. Each clamp arm 7a, 7b is provided with a guide groove 11, and the guide grooves 11 of the clamp arms 7a, 7b partially overlap each other. The clamp device 3 further includes a guide pin 12, which is attached to the clamp base 6 and extends through the guide grooves 11 in overlapping parts thereof, so that by the engagement of the guide pin 12 and the guide grooves 11 a movement of the control wire 4 in the proximal direction is translated into a closing movement of the clamp arms 7a, 7b, and a movement of the control wire 4 in a distal direction is translated into an opening movement of the clamp arms 7a, 7b around the pivot axis. In the present embodiment, the guide pin 12 is held between two bearing arms 13a, 13b extending upright from the distal end of the clamp base 6 forming a bifurcated structure, the clamp arm 7a, 7b being arranged between those bearing arms 13a, 13b extending laterally outward of the structure. The clamp base 6 and the bearing arms 13a, 13b together form a clamp housing.

Figure 3:
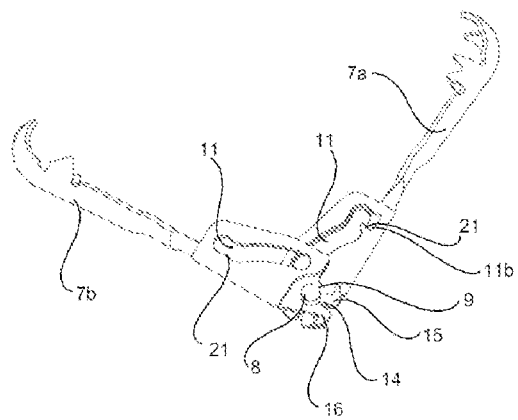
FIG. 3 is a view illustrating clamp arms connected by a pivot pin in the medical device in fully open state.
Figure 4:
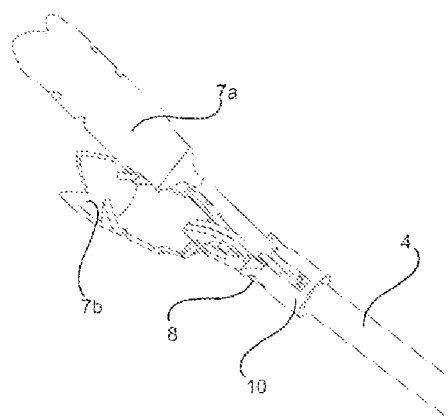
FIG. 4 shows a perspective view of the distal part of the medical device with a clamp device.
Figure 5:
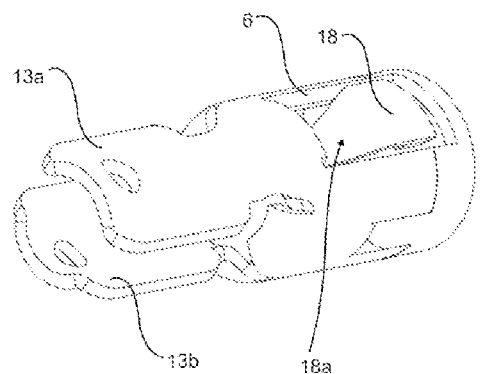
FIG. 5 shows an enlarged perspective view of a clamp base of the clamp device.
Figure 6:
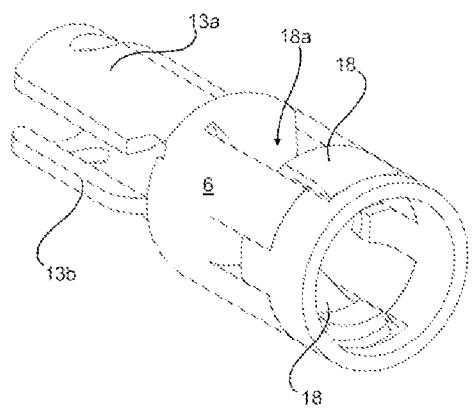
FIG. 6 shows another enlarged perspective view of the clamp base of the clamp device.
Figure 7:
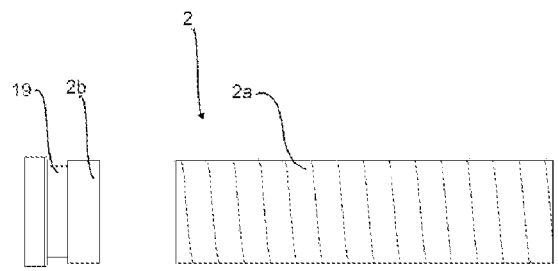
FIG. 7 shows a sheath device of the medical device with a coiled sheath and a connect tube, FIG. 8 corresponds to FIG. 7 and shows the connect tube mounted to the sheath.
Figure 8:
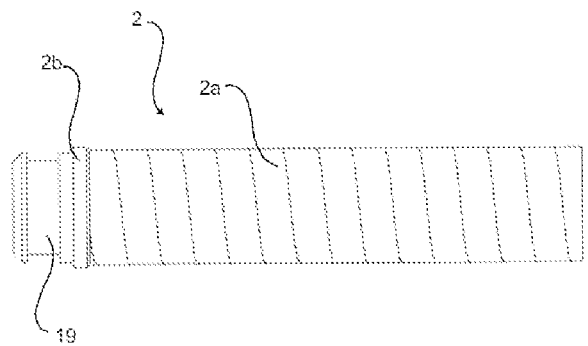
Figure 9:
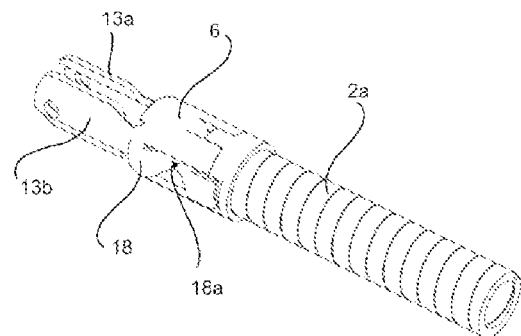
FIG. 9 is a perspective view showing the clamp base attached to the sheath device.
Figure 10:
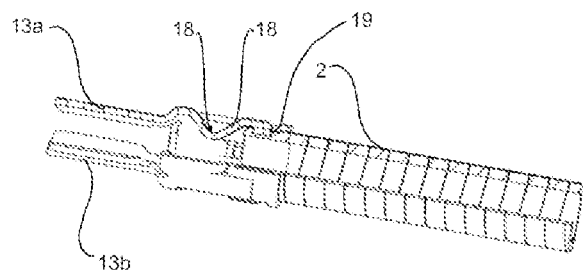
FIG. 10 is a partially sectioned view of the arrangement in FIG. 9.
Figure 11:
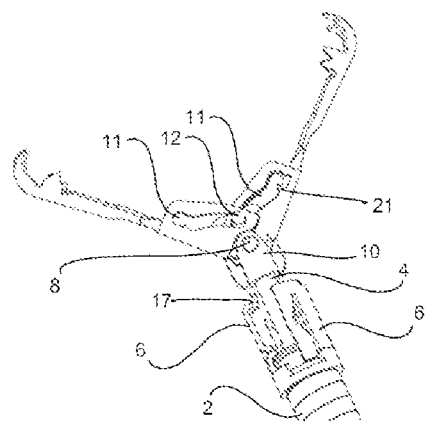
FIG. 11 is a partially sectioned view of the clamp device with the clamp arms in fully open state.
Figure 12:
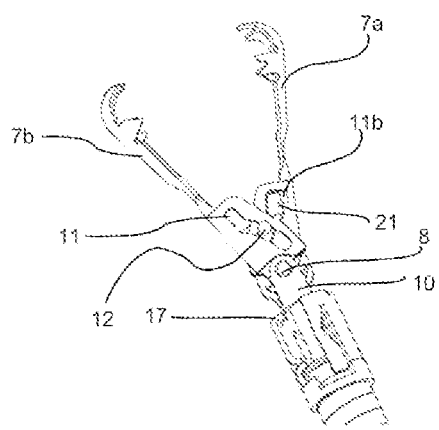
FIG. 12 is a partially sectioned view of the clamp device with partially closed clamp arms.
Figure 13:
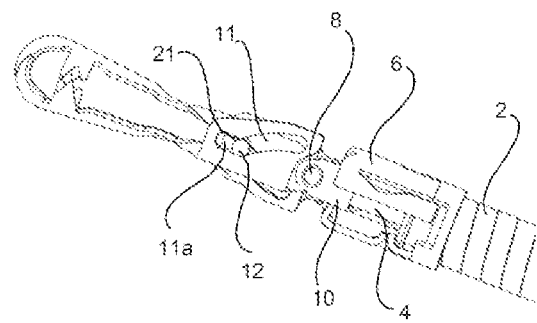
FIG. 13 is a partially sectioned view of the clamp device with closed clamp arms, FIG. 14 corresponds to FIG. 13 without sections, FIG. 15 corresponds to FIG. 13 and shows the arrangement with further retracted control wire, FIG. 16 corresponds to FIG. 15 with the clamp base in sectional view and the clamp arms in fully closed and secured position.
Figure 14:
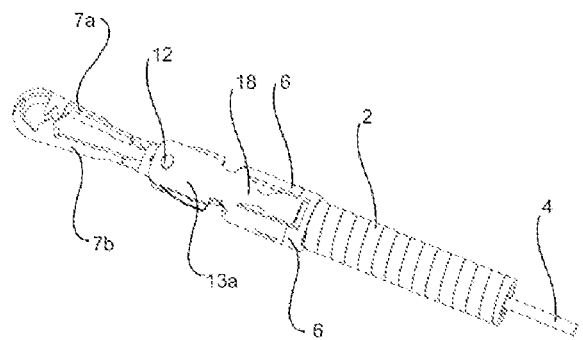
Figure 15:
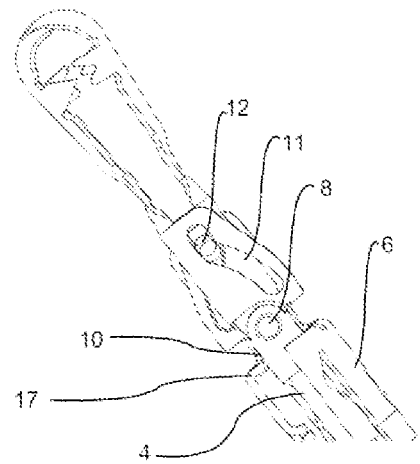
Figure 16:
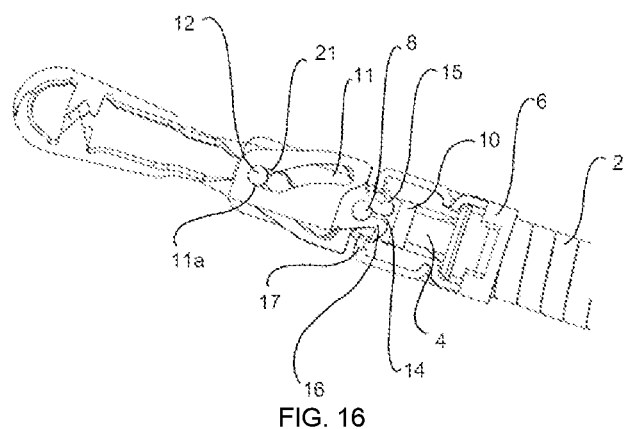

As in particular shown in FIG. 3, the through-holes 9 for the pivot pin 8 in the proximal end sections of the clamp arms 7a, 7b are open to their rear (proximal) side. In other words, exit-passages 14 are provided in tail ends of the clamp arms 7a, 7b at proximal sides of the through-holes 9, through which after closing the clamp arms 7a, 7b the pivot pin 8 can be pulled out of the through-holes 9 spreading apart the tail end sections 15, 16 of the clamp arms 7a, 7b on opposite sides of the openings without breaking. In this way the control wire 4 is uncoupled from the clamp arms 7a, 7b and accordingly the clamp device 3. The exit-passages 14 are here formed by slits in the tail ends of the clamp arms 7a, 7b.

In this embodiment, the tail end sections 15, 16 of the clamp arms 7a, 7b are plastically deformed, when they are spread apart and formed as hooks, which are to be brought into engagement behind a shoulder 17 of the clamp base 6 in order to lock the clamp arms 7a, 7b therein, as will be explained in detail later. The shoulder 17 is formed by an annular, inwardly directed projection that is provided at the distal end of the clamp base 6 and forms a distal end surface thereof.

The sheath device 2 includes a coiled sheath 2a, which is connected to the handle 1, and a connect tube 2b, which is provided on a distal end of the coiled sheath 2a and laser welded thereto, so that the sheath device 2 forms an inseparable unit. The sheath device 2 is connected to the clamp base 6 by means of two connecting elements 18 in the form of elastic connecting arms that are formed in a one piece construction with the clamp base 6 on opposite sides thereof. Specifically, the distal ends of the connecting elements 18 are fixedly connected to the clamp base 6, whereas free proximal ends of the connecting elements 18 form engagement portions that engage corresponding engagement means provided on a circumferential surface of the connect tube 2b, in order to couple the clamp base 6 to the sheath device 2. Here the engagements portions of the connecting elements 18 are formed as inwardly directed engagement portions, which engage a ring groove 19 which is provided as engagement means in an outer surface of the connect tube 2b, in order to couple the clamp base 6 to the sheath device 2.

Figure 2:
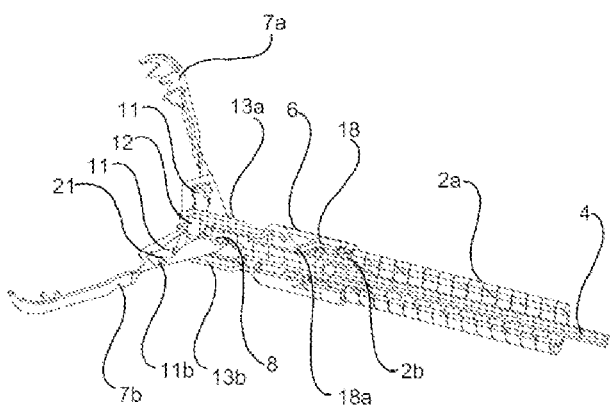
FIG. 2 shows in enlarged scale a front, distal part of the medical device in FIG. 1 in partially sectioned view.

As obtainable from FIG. 2, a distal end of the connect tube 2b extends into the sleeve-like clamp base 6, so that the ring groove 19 is positioned within the clamp base 6.

The connecting elements 18 have inwardly bulged sections 18a in their middle portions. These inwardly bulged sections 18a cooperate with a protrusion 20 of the control wire 4, which forms part of a release arrangement and can be actuated by movement of the control wire 4 in the proximal direction in order to release the clamp base 6 from the sheath device 2, when the clamp arms 7a, 7b have been closed. In detail the protrusion 20 is formed by a rear, proximal part of the coupling head 10 of the control wire 4 and provided to come into engagement with the inwardly bulged sections 18a of the connecting elements 18, so that when the control wire 4 is pulled in proximal direction the bulged sections 18a of the connecting elements 18 are plastically deformed outwardly by the engagement with the protrusions 20 and thus the free ends of the connecting elements 18 are disengaged from the ring groove 19 of the connect tube 2b.

In use the clamp device 3 is delivered to a target site through an endoscope, and the clamp device 3 is fixed at a predetermined position on the target site to a blood vessel. In order to pinch the blood vessel the clamp arms 7a, 7b can be repeatedly opened and closed by moving the control wire 4 in the distal and proximal directions by means of the actuator 5.

Figure 17:
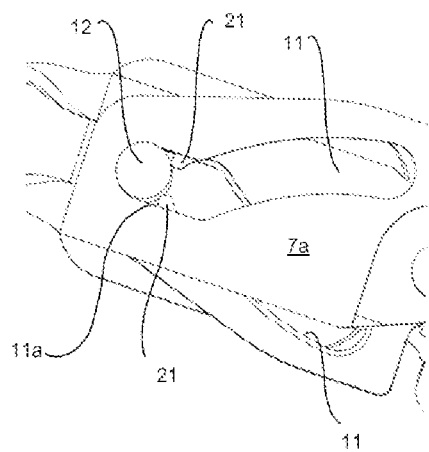
FIG. 17 shows engagement of a guide pin and guide grooves of the clamp arms in a position of FIG. 16 in enlarged scale, FIG. 18 to FIG. 20 correspond to FIG. 15 and FIG. 16 and show a process of uncoupling the control wire from the clamp arms.
Figure 18:
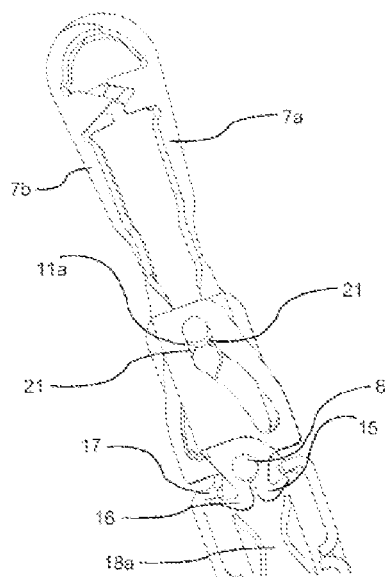
Figure 19:
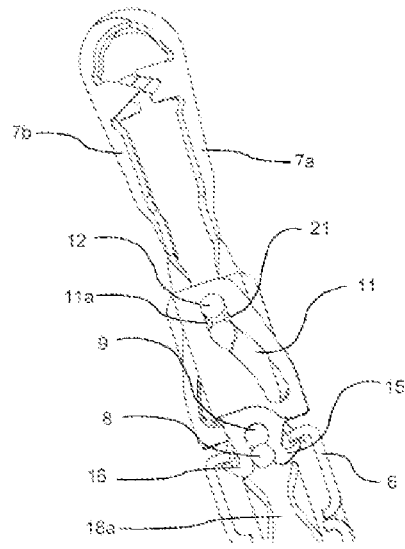
Figure 20:
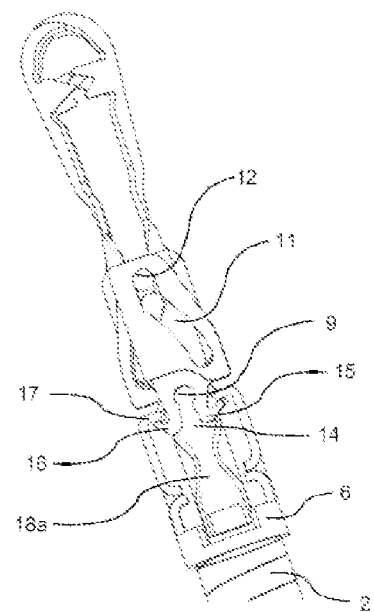
Figure 21:
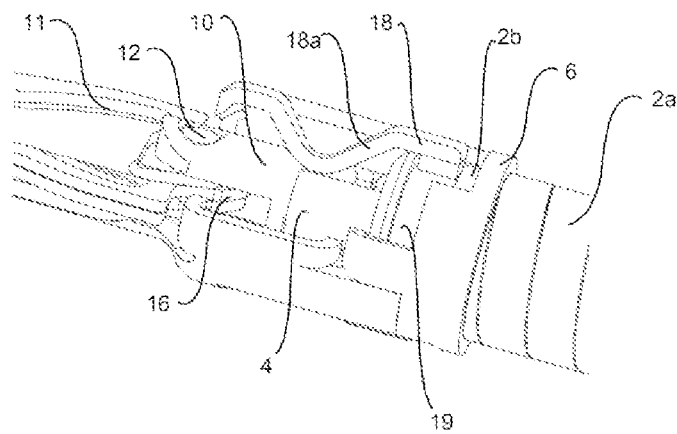
FIG. 21 to FIG. 23 are partially sectioned views of the clamp base showing release of the clamp base from the sheath device.
Figure 22:
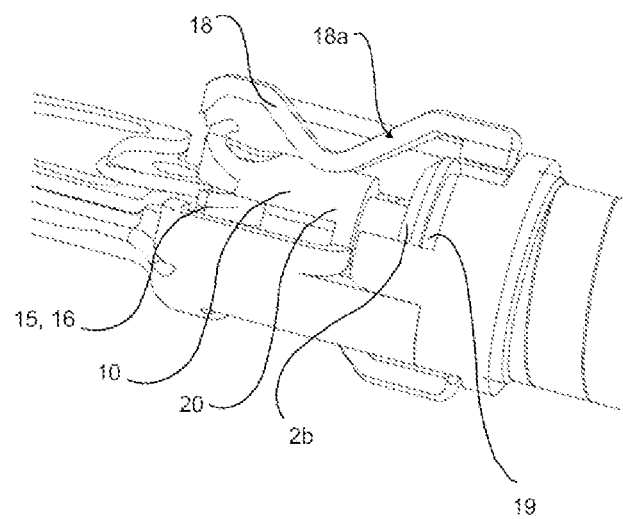
Figure 23:
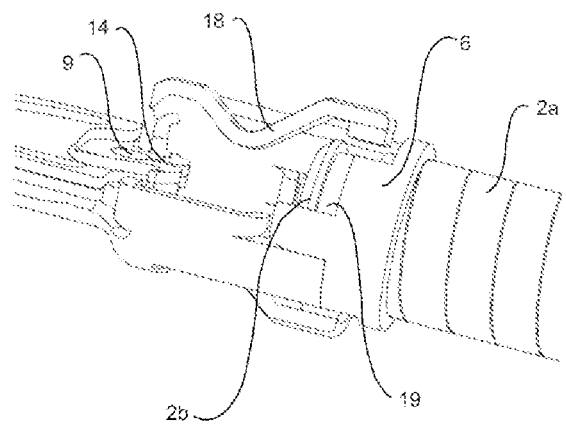
Figure 24:
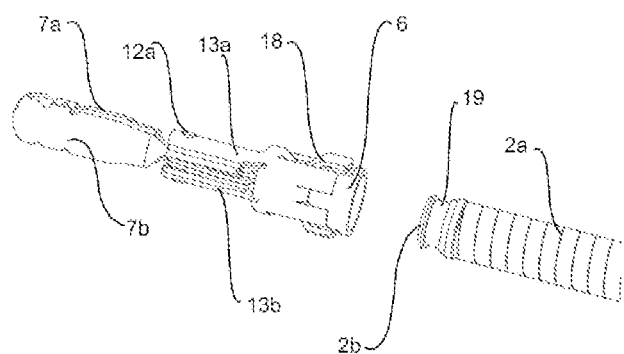
FIG. 24 is a perspective view showing the clamp device separated from the sheath device.
Figure 25:
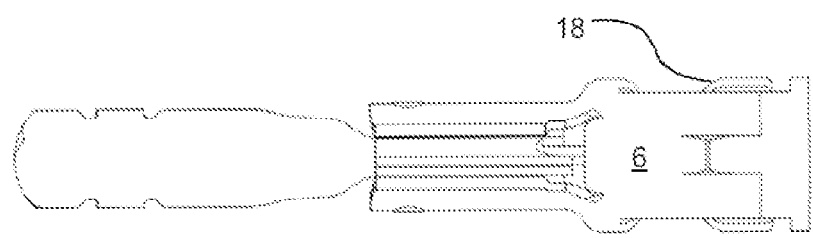
FIG. 25 and FIG. 26 are top views of the clamp base before and after disconnecting from the sheath device.
Figure 26:
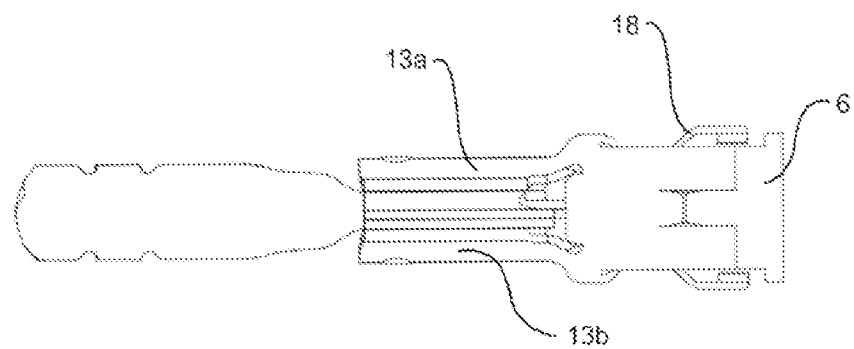
Figure 27:
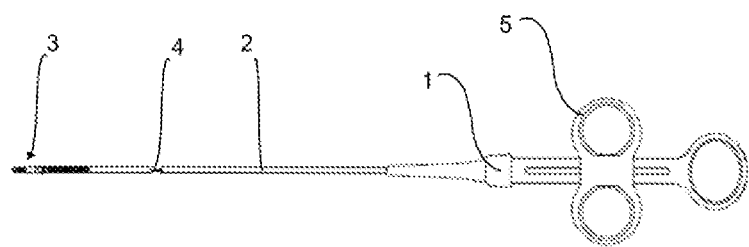
FIG. 27 shows a front view of a medical device according to another embodiment of the present disclosure.

Once the clamp device 3 has been set the clamp arms 7a, 7b are to be disconnected from the control wire 4. For this purpose the control wire 4 is pulled in the proximal direction in order to fully close the clamp arms 7a, 7b and secure them in the closed position, as depicted in FIG. 17 to FIG. 19. These figures show that the guide grooves 11 have a straight, axially extending distal end section 11a, in which the guide pins 12 can move without incurring further rotation of the clamp arms 7a, 7b. When the guide pins 12 reach their front, distal end positions in the guide grooves 11, they are secured/locked in this position by holding noses 21 provided on the clamp arms 7a, 7b. The holding noses 21 extend into the straight end sections 11a of the guide grooves 11 from a lateral side thereof and are designed in such a way, that the holding noses allow the guide pins 12 to pass them to reach the proximal ends of the guide grooves 11 but prevent passing of the guide pins 12 in an opposite direction. Specifically the holding noses 21 are designed such that the holding noses elastically deform into recesses 11b in lateral sides of the guide grooves 11 when the guide pins 12 press against their proximal side, to allow the guide pins 12 to pass the holding noses 21 and reach their distal end positions in the guide grooves 11, that the holding noses regain their initial form by their elastic restoring force to engage behind the guide pins 12, when the guide pins 12 have reached their final positions, but that the holding noses cannot be deformed to open the guide grooves 11 when the guide pins 12 press against their distal side, so that the guide pins 12 are captured in their distal end positions in the guide grooves 11. In this way the clamp arms 7a, 7b are securely locked to the clamp base 6 and accordingly the clamp housing.

If the control wire 4 is further pulled back, a further transitional movement of the clamp arms 7a, 7b is no more possible, and insofar the pivot pin 8 is pulled out of the through-holes 9 through the exit-passages 14 on the rear side thereof. During this process the tail end sections 15, 16 located on the opposite sides of the exit-passages 14 are plastically spread apart to engage behind the shoulder 17 of the clamp base 6, thus locking the clamp arms 7a, 7b to the clamp base 6.

In order to uncouple/release the clamp base 6 from the sheath device 2, the control wire 4 is further pulled back in proximal direction, so that the protrusion 20 of the coupling head 10 comes into engagement with the inwardly bulged sections 18a of the connecting elements 18 (see FIG. 23a) and pushes the bulged sections 18a outwardly plastically deforming them, thus bringing the free ends of the connecting elements 18 out of engagement from the ring groove 19 of the connect tube 2b (FIGS. 23b, 23c), so that the clamp device 3 with the clamp base 6 and the clamp arms 7a, 7b can be pulled from the sheath device 2.

FIG. 27 to FIG. 53 show an embodiment of a medical device according to another embodiment of the present disclosure. The basic design of this embodiment corresponds to the previous embodiment. These embodiments only differ in the specific ways, in which the control wire 4 is coupled to the clamp arms 7a, 7b and the design and function of the connecting elements 18.

The medical device according to this embodiment includes a handle 1, a sheath device 2, which is attached to the handle 1, and a clamp device 3 which is provided on the distal end of the sheath device 2. A control wire 4 extends through the sheath device 2 and is at its proximal end connected to an actuator 5, which is slidingly held on the handle 1 and can be actuated to reversibly move the control wire 4 in the distal and proximal directions.

The clamp device 3 includes a clamp base 6 formed as a sleeve and two clamp arms 7a, 7b, which are each coupled to the distal end of the control wire 4. Specifically the two clamp arms 7a, 7b are separate elements/components that are coupled to the control wire 4 by means of a pivot pin 8, which is provided at a distal end section of the control wire 4 and extends through corresponding through-holes 9 provided in proximal end sections of the clamp arms 7a, 7b. In the present embodiment the pivot pin 8 is provided on a coupling head 10, which is provided at the distal end of the control wire 4. In this embodiment the coupling head 10 is flat and arranged between the clamp arms 7a, 7b, and the pivot pin 8 has two pivot pin sections 8a, 8b extending from opposite sides of the coupling head 10 to engage the respective through-holes 9 in the clamp arms 7a, 7b.

The two clamp arms 7a, 7b are coupled to the distal end of the control wire 4 so that they can be rotated around a common pivot axis formed by the pivot pin 8 to open and close the clamp arms 7a, 7b.

Each clamp arm 7a, 7b is provided with a guide groove 11, and the guide grooves 11 of the clamp arms 7a, 7b partially overlap each other. The clamp device 3 further includes a guide pin 12, which is attached to the clamp base 6 and extends through the guide grooves 11 in the overlapping parts thereof, so that by the engagement of the guide pin 12 and the guide grooves 11 a movement of the control wire 4 in the proximal direction is translated into a closing movement of the clamp arms 7a, 7b, and a movement of the control wire 4 in a distal direction is translated into an opening movement of the clamp arms 7a, 7b around the pivot axis. In the present embodiment, the guide pin 12 is held between two bearing arms 13a, 13b extending upright from the distal end of the clamp base 6 forming a bifurcated structure, the clamp arm 7a, 7b being arranged between those bearing arms 13a, 13b extending laterally outward of the structure. The clamp base 6 and the bearing arms 13a, 13b together form a clamp housing.

The through-holes 9 for the pivot pin 8 in the proximal end sections of the clamp arms 7a, 7b are open to their rear (proximal) side. In other words, exit-passages 14 are provided in tail ends of the clamp arms 7a, 7b at the proximal sides of the through-holes 9, through which after closing the clamp arms 7a, 7b the pivot pin 8 can be pulled out of the through-holes 9 spreading apart the tail end sections 15, 16 of the clamp arms 7a, 7b on opposite sides of the openings without breaking. In this way the control wire 4 is uncoupled from the clamp arms 7a, 7b and accordingly the clamp device 3. The exit-passages 14 are here formed by slits in the tail ends of the clamp arms 7a, 7b.

Figure 44:
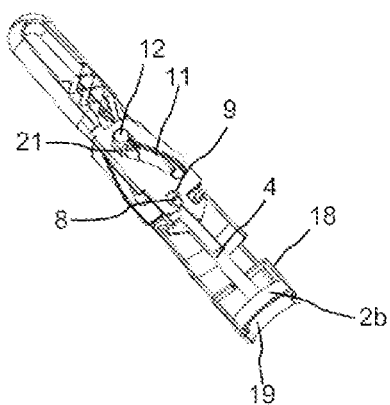
FIG. 44 and FIG. 45 are partially sectioned views showing a process of uncoupling the control wire from the clamp arms after securing the clamp arms in the closed state, FIG. 46 and FIG. 47 correspond to FIG. 41 and FIG. 42 and show a process of closing the clamp arms and securing them in the closed state and simultaneously uncoupling the control wire from the clamp arms.
Figure 45:
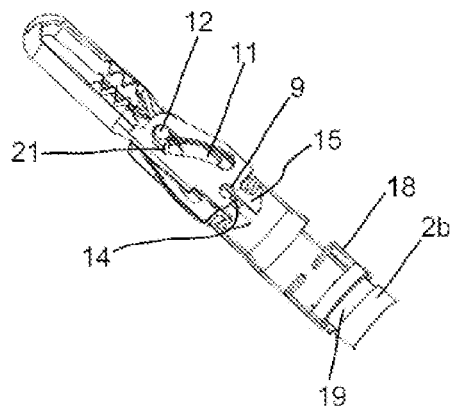

In this embodiment the tail end sections 15, 16 of the clamp arms 7a, 7b are elastically deformed, when they are spread apart, and they are formed as hooks, which engage behind a shoulder 17 of the clamp base 6 in order to lock the clamp arms 7a, 7b therein. The shoulder 17 is formed by an annular, inwardly directed projection that is provided at the distal end of the clamp base 6 and forms the distal end surface thereof (FIG. 44 and FIG. 45).

The sheath device 2 includes a coiled sheath 2a, which is connected to the handle 1, and a connect tube 2b, which is provided on a distal end of the coiled sheath 2a and laser welded thereto, so that the sheath device 2 forms an inseparable unit. The sheath device 2 is connected to the clamp base 6 by means of two connecting elements 18 in the form of elastic connecting arms that are formed in a one piece construction with the clamp base 6 on opposite sides thereof. Specifically, the distal ends of the connecting elements 18 are fixedly connected to the clamp base 6, whereas free proximal ends of the connecting elements 18 form engagement portions that engage corresponding engagement means provided on a circumferential surface of the connect tube 2b, in order to couple the clamp base 6 to the sheath device 2. Here the engagements portions of the connecting elements 18 are formed as inwardly directed engagement portions, which engage a ring groove 19 which is provided as engagement means in an outer surface of the connect tube 2b, in order to couple the clamp base 6 to the sheath device 2.

Figure 28:
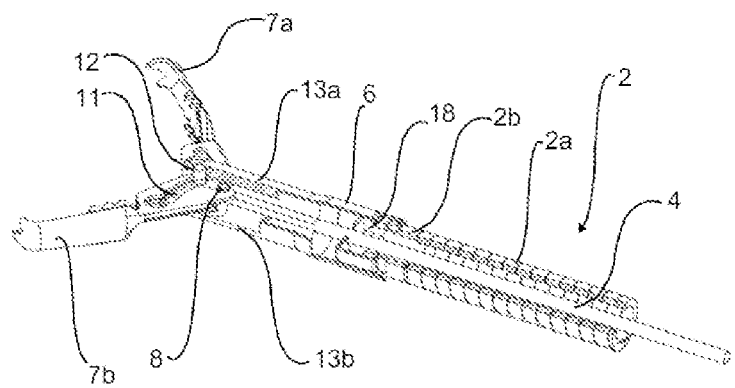
FIG. 28 shows in enlarged scale a front, distal part of the medical device in FIG. 27 in partially sectioned view.
Figure 29:
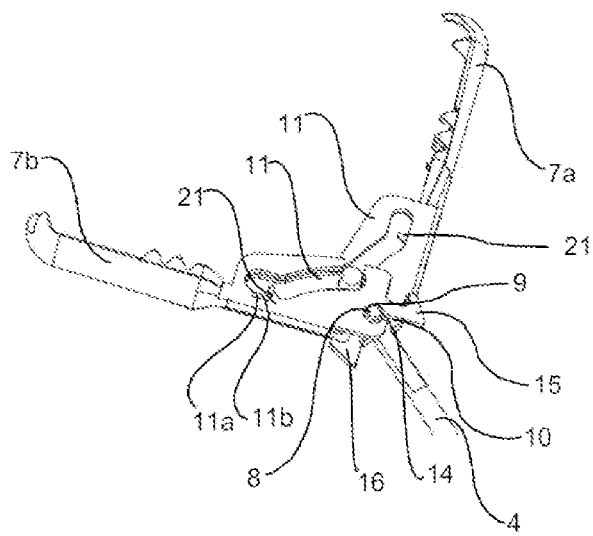
FIG. 29 is a view showing the clamp arms of the medical device connected by a pivot pin in fully open state.
Figure 30:
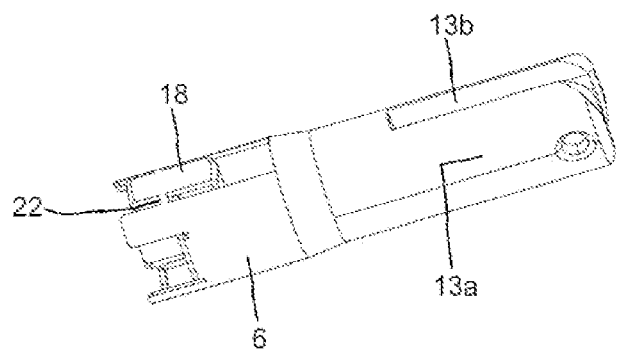
FIG. 30 shows an enlarged perspective view of the clamp base of the clamp device.
Figure 31:
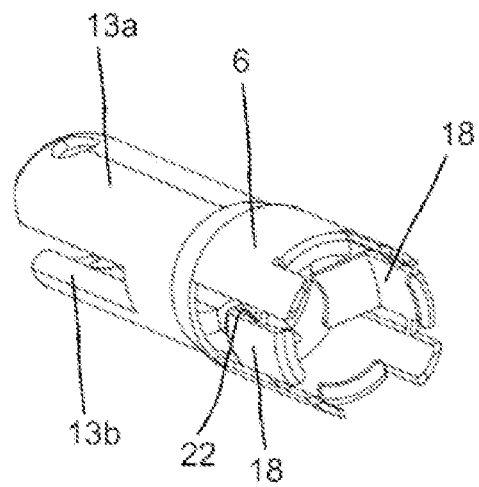
FIG. 31 shows another enlarged perspective view of the clamp base of the clamp device.
Figure 32:
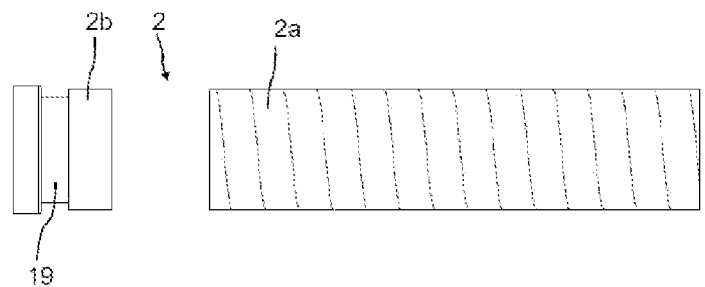
FIG. 32 shows the sheath device of the medical device with a coiled sheath and a connect tube, FIG. 33 corresponds to FIG. 32 and shows the connect tube mounted to the sheath.
Figure 33:
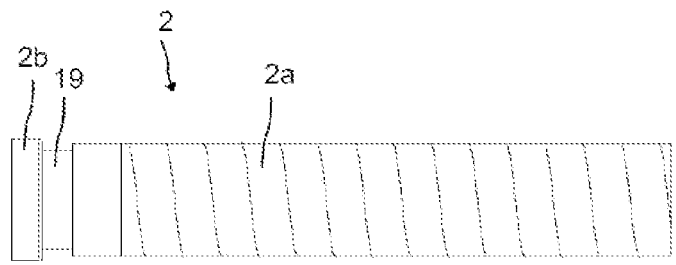
Figure 34:
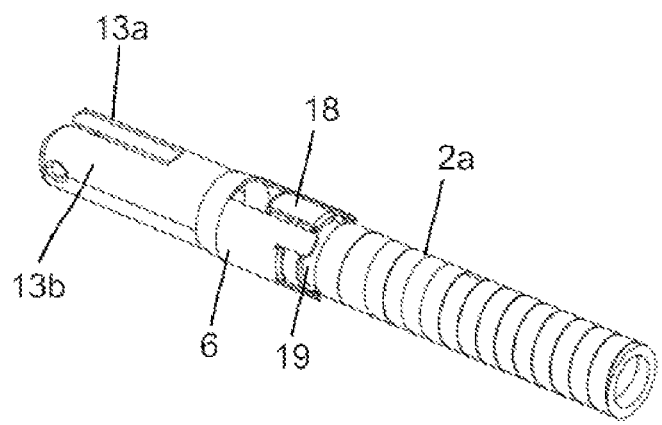
FIG. 34 is a perspective view showing the clamp base attached to the sheath device.
Figure 40:
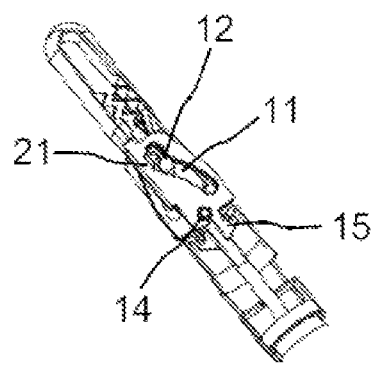
Figure 41:
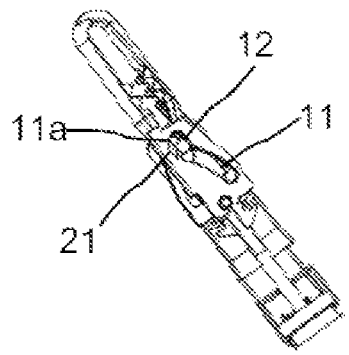
Figure 42:
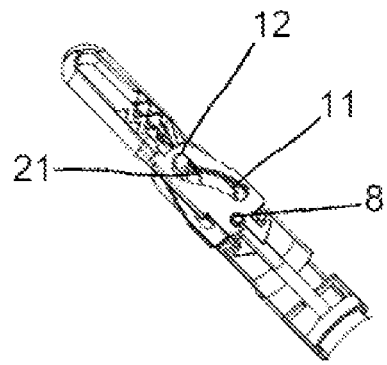
Figure 43:
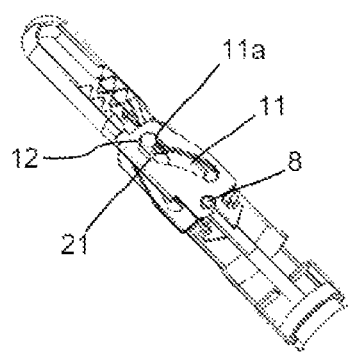
FIG. 43 shows the arrangement of FIG. 42 in enlarged scale.

As obtainable from FIG. 28, a distal end of the connect tube 2b extends into the sleeve-like clamp base 6, so that the ring groove 19 is positioned within the clamp base 6.

The connecting elements 18 of this embodiment are formed as C-shaped connecting arms, wherein a central bar of the C-shaped connecting arm is attached at a connection site on opposite sides thereof to the clamp base 6 by two plastically deformable narrow webs 22, a distal C-leg extends inwardly into the clamp base 6, so that it can be engaged by the protrusion 20, and the other proximal C-leg forming the engagement portion extends inwardly to engage the ring groove 19 of the connect tube 2b. The arrangement is such that if in the closed position of the clamp arms 7a, 7b the control wire 4 is pulled in a proximal direction, the protrusion 20 engages the distal C-legs so that the connecting elements 18 are pivoted around their connection sites defined by the opposing webs 22 to move the proximal C-legs out of engagement from the ring groove 19. (see FIG. 48 to FIG. 50)

In use the clamp device 3 is delivered to a target site through an endoscope, and the clamp device 3 is fixed at a predetermined position on the target site to a blood vessel. In order to pinch the blood vessel the clamp arms 7a, 7b can be repeatedly opened and closed by moving the control wire 4 in the distal and proximal directions by means of the actuator 5.

Once the clamp device 3 has been set the clamp arms 7a, 7b are to be disconnected from the control wire 4. For this purpose the control wire 4 is pulled in the proximal direction in order to fully close the clamp arms 7a, 7b and secure them in the closed position, as depicted in FIG. 17 to FIG. 19. These figures show that the guide grooves 11 have a straight, axially extending distal end section 11a, in which the guide pins 12 can move without incurring further rotation of the clamp arms 7a, 7b. When the guide pins 12 reach their front, distal end positions in the guide grooves 11, they are secured/locked in this position by holding noses 21 provided on the clamp arms 7a, 7b. The holding noses 21 extend into the straight end sections 11a of the guide grooves 11 from a lateral side thereof and are designed in such a way, that the holding noses allow the guide pins 12 to pass them to reach the proximal ends of the guide grooves 11 but prevent passing of the guide pins 12 in an opposite direction. Specifically the holding noses 21 are designed such that the holding noses elastically deform into recesses 11b in lateral sides of the guide grooves 11 when the guide pins 12 press against their proximal side, to allow the guide pins 12 to pass the holding noses 21 and reach their distal end positions in the guide grooves 11, that the holding noses regain their initial form by their elastic restoring force to engage behind the guide pins 12, when the guide pins 12 have reached their final positions, but that the holding noses cannot be deformed to open the guide grooves 11 when the guide pins 12 press against their distal side, so that the guide pins 12 are captured in their distal end positions in the guide grooves 11. In this way the clamp arms 7a, 7b are securely locked to the clamp base 6 and accordingly the clamp housing. (see FIG. 42)

If the control wire 4 is further pulled back, a transitional movement of the clamp arms 7a, 7b is no more possible, and insofar the pivot pin 8 is pulled out of the through-holes 9 through the exit-passages 14 on the rear side thereof. During this process the tail end sections 15, 16 located on the opposite sides of the exit-passages 14 are elastically spread apart to open the exit-passages, but return in their original form once the pivot pin 8 has left the exit-passages 14. In order to uncouple/release the clamp base 6 from the sheath device 2, the control wire 4 is further pulled back in the proximal direction, so that the protrusion 20 of the coupling head 10 comes into engagement with the inwardly directed distal C-legs of the connecting elements 18 (see FIG. 23a) and pushes these C-legs in the proximal direction with the result, so that the connecting elements 18 are pivoted around the connection site defined by the opposing webs 22 to move the proximal C-leg out of engagement from the ring groove 19. (FIG. 48 to FIG. 56)

During the closing process of the clamp arms 7a, 7b the tail ends of the clamp arms 7a, 7b enter the clamp base 6 through a central opening of the ring shaped shoulder 17. As obtainable from FIG. 36 to FIG. 38 lateral extension of the clamp arms 7a, 7b exceeds a diameter of the opening, so that the clamp arms 7a, 7b are elastically compressed when they enter the clamp base 6 and after re-expansion engage behind the shoulder 17 of the clamp base 6 in order to lock the clamp arms 7a, 7b to the clamp base 6.

Figure 46:
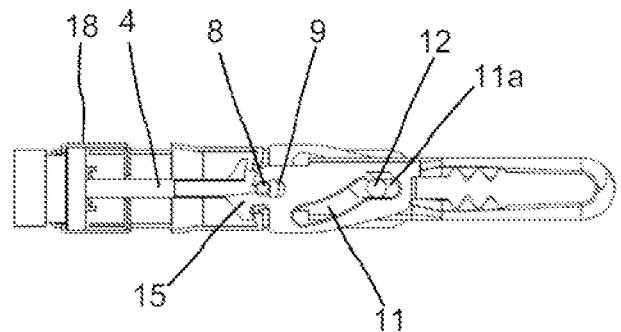
Figure 47:
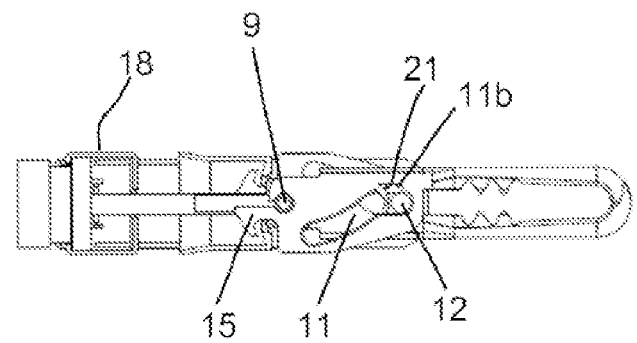
Figure 48:
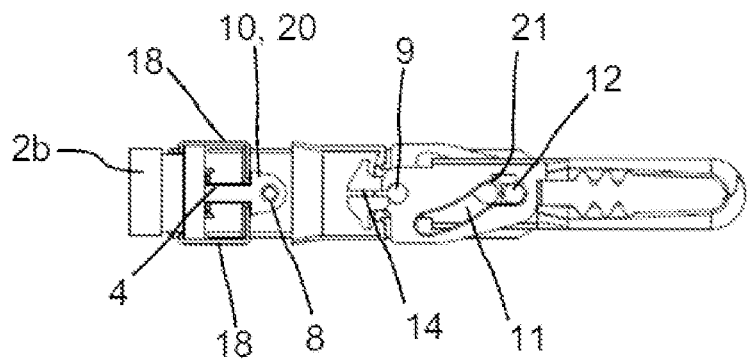
FIG. 48 to FIG. 50 are partially sectioned views of the clamp base showing release of the clamp base from the sheath device.
Figure 49:
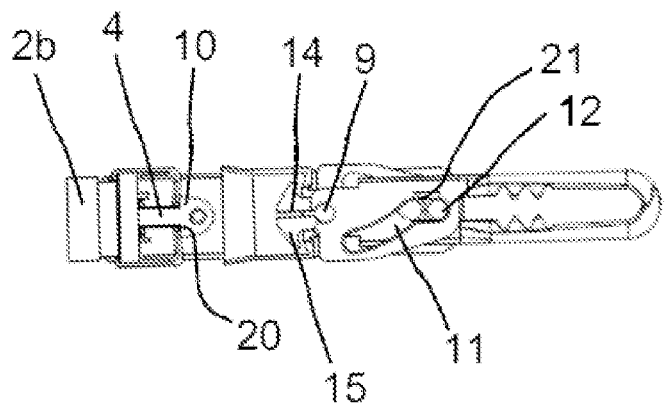
Figure 50:
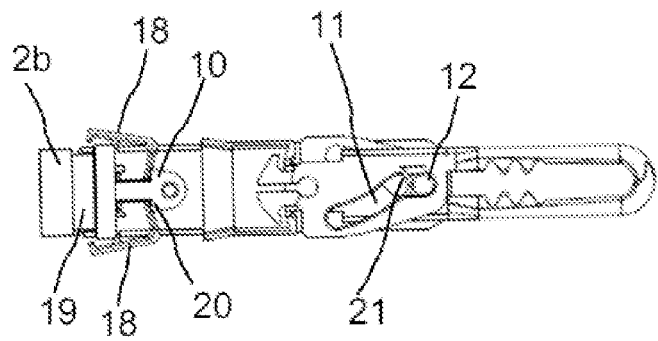
Figure 51:
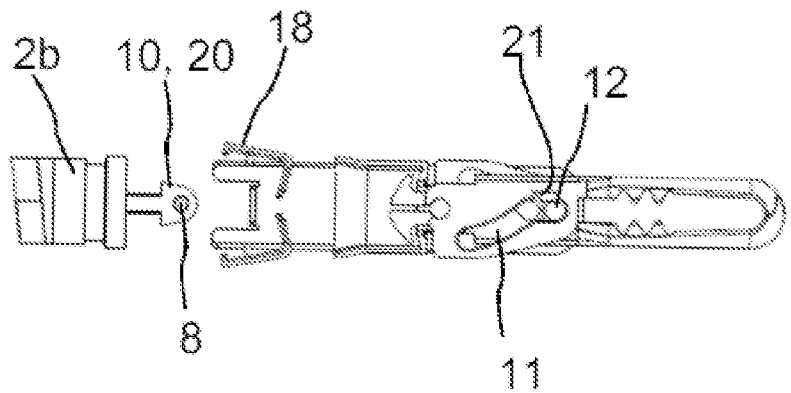
FIG. 51 is a perspective view showing the clamp device separated from the sheath device.
Figure 52:
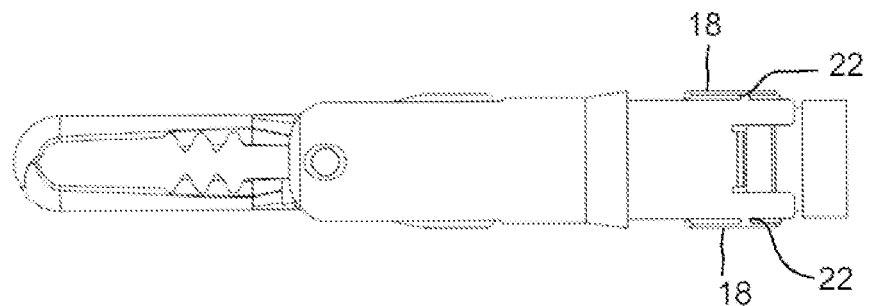
FIG. 52 and FIG. 53 are top views of the clamp base before and after disconnecting from the sheath device.
Figure 53:
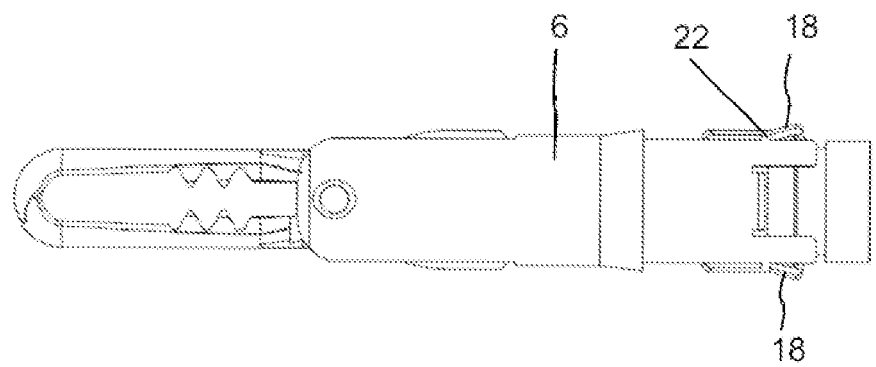
Figure 54:
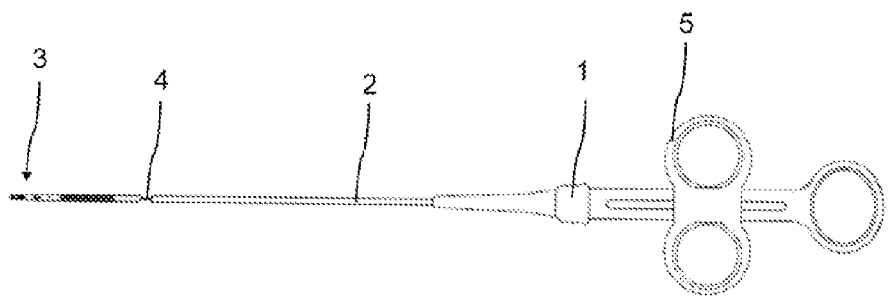
FIG. 54 shows a front view of a medical device according to a further embodiment of the present disclosure.
Figure 55:
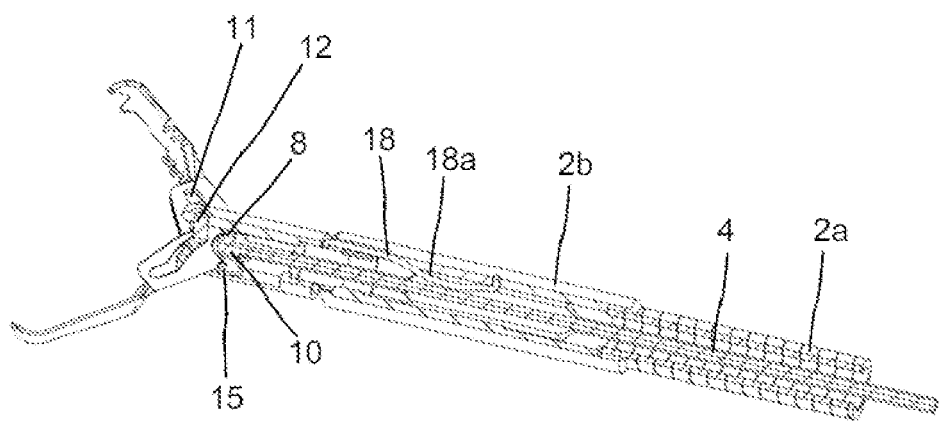
FIG. 55 shows in enlarged scale the front, distal part of the medical device in FIG. 54 in partially sectioned view.
Figure 56:
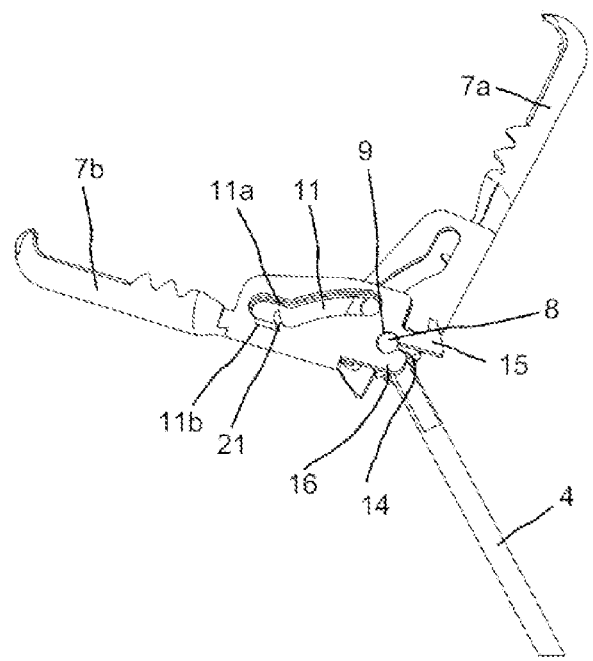
FIG. 56 is a view showing the clamp arms of the medical device operatively connected to each other by a pivot pin in fully open state.
Figure 57:
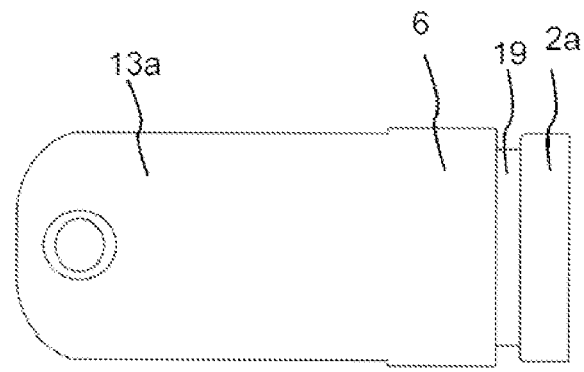
FIG. 57 shows an enlarged perspective view of the clamp base of the clamp device.
Figure 58:
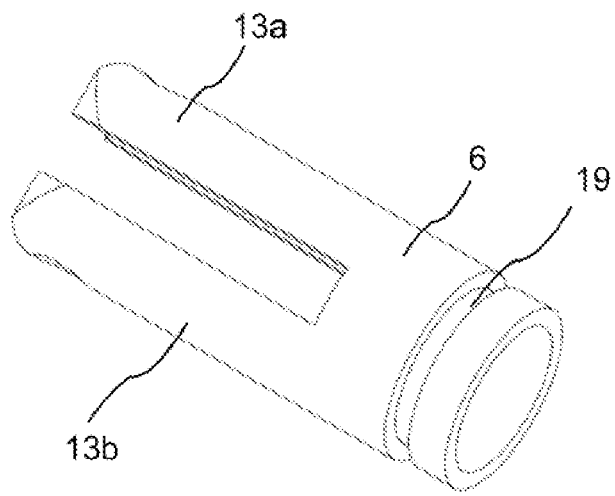
FIG. 58 shows a further enlarged perspective view of the clamp base of the clamp device.
Figure 59:
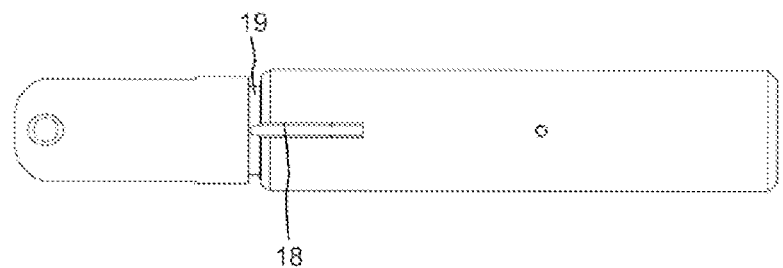
FIG. 59 is a view showing the clamp base attached to the sheath device.
Figure 60:
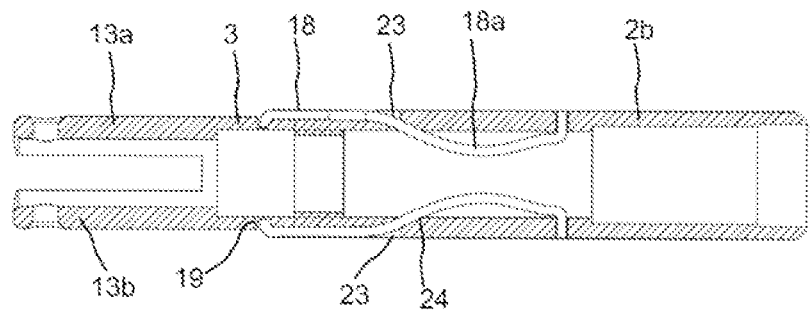
FIG. 60 is a sectioned view of the arrangement of FIG. 59.
Figure 61:
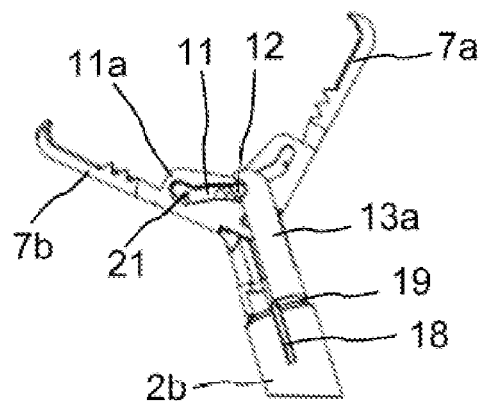
FIG. 61 is a partially sectioned view of the clamp device with the clamp arms in fully open state.
Figure 62:
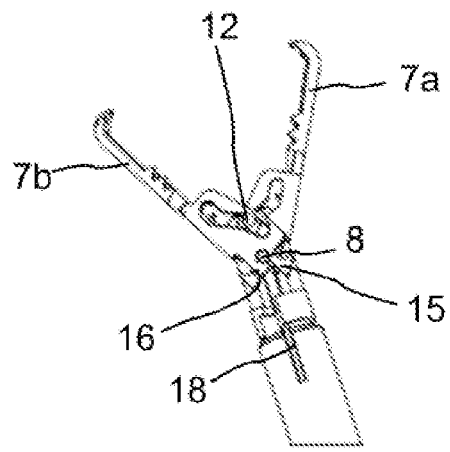
FIG. 62 is a partially sectioned view of the clamp device with partially closed clamp arms.
Figure 63:
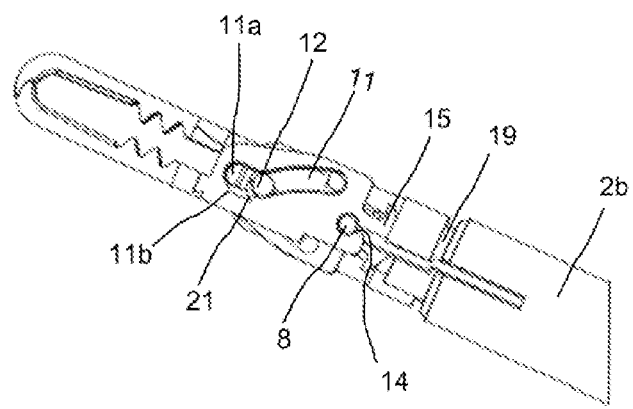
FIG. 63 is a partially sectioned view of the clamp device with closed clamp arms, FIG. 64 corresponds to FIG. 63 and shows the arrangement with further retracted control wire, FIG. 65 corresponds to FIG. 64 with the clamp base in sectional view and the clamp arms in fully closed and secured position.
Figure 64:
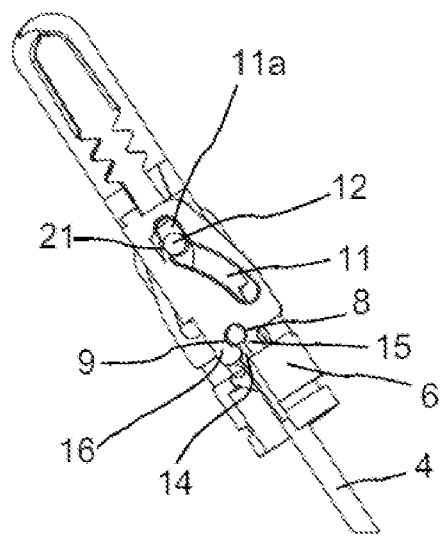
Figure 65:
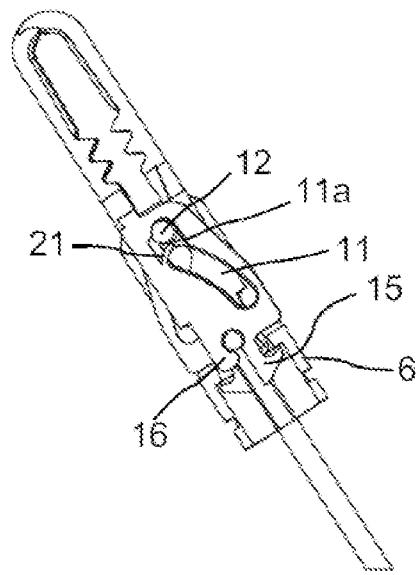
Figure 66:
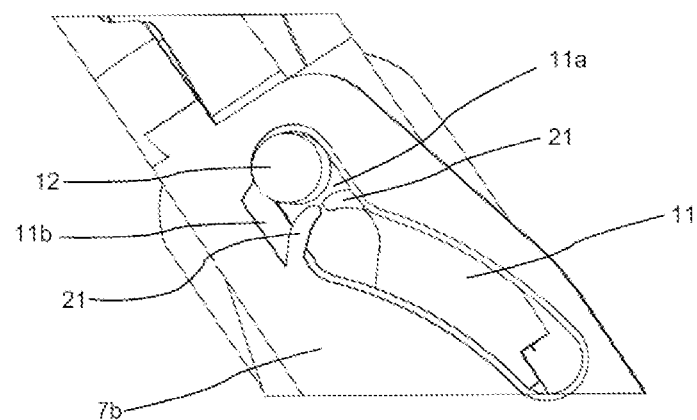
FIG. 66 shows engagement of the guide pin and the guide groove of the clamp arms in the position of FIG. 65 in enlarged scale, FIG. 67 to FIG. 69 correspond to FIG. 64 and show the process of uncoupling the control wire from the clamp arms.
Figure 67:
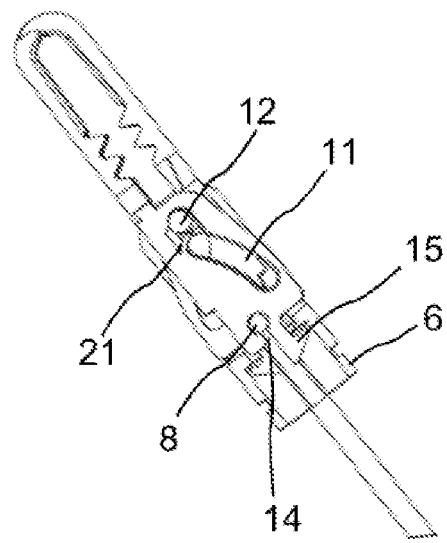
Figure 68:
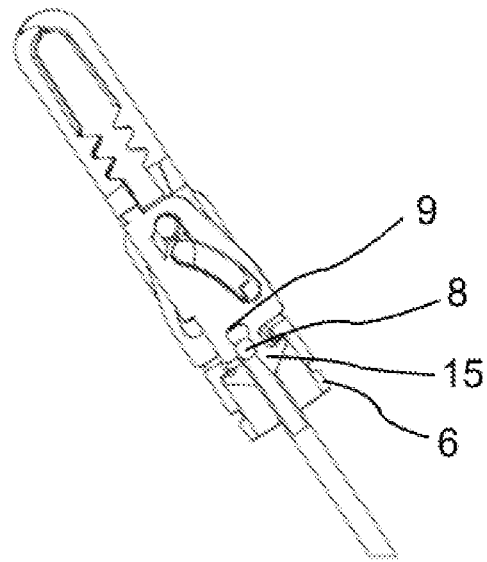
Figure 69:
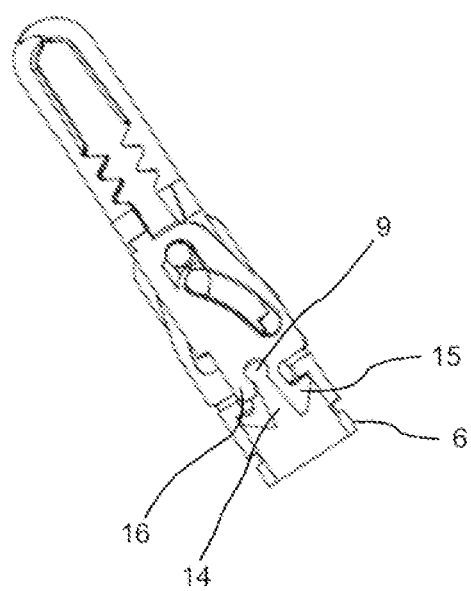
Figure 70:
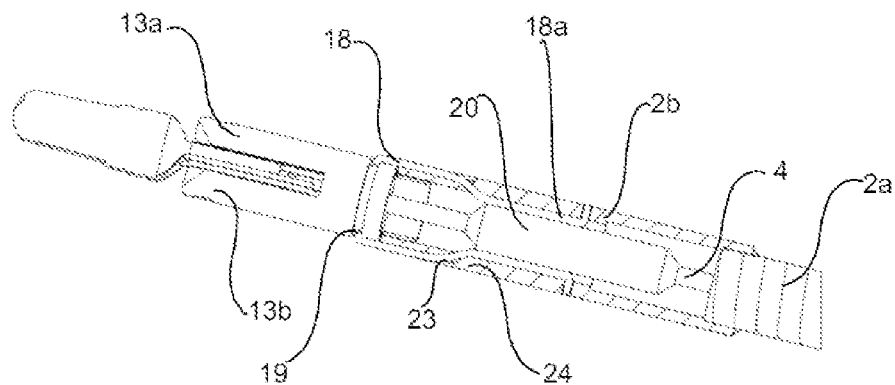
FIG. 70 and FIG. 71 are partially sectioned views of the clamp base showing the release of the clamp base from the sheath device.
Figure 71:
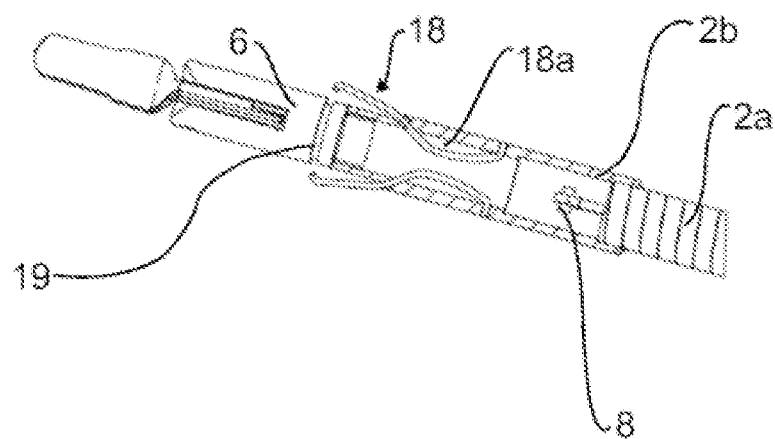
Figure 72:
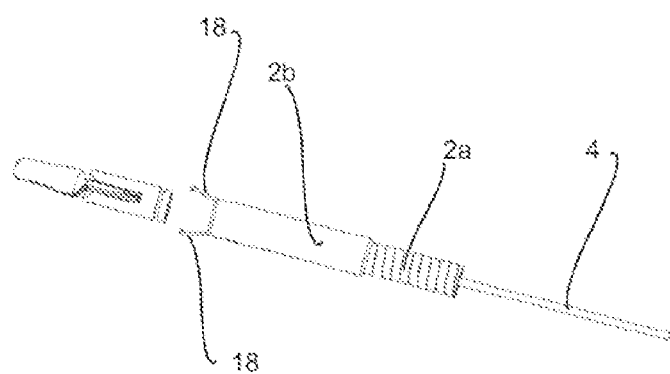
FIG. 72 is a perspective view showing the clamp device separated from the sheath device.
Figure 73:
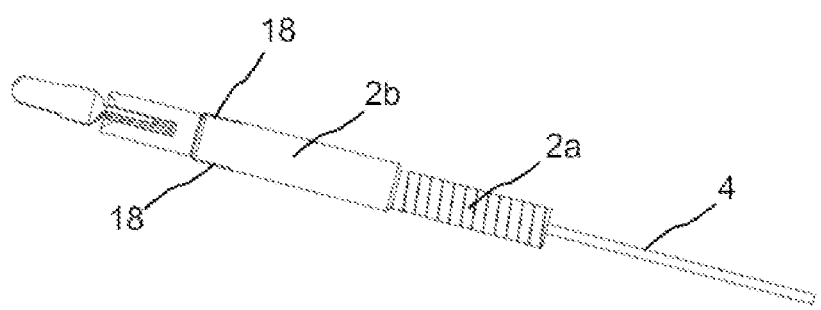
FIG. 73 is a top view of the clamp base before disconnecting from the sheath device.

As shown in FIG. 46 and FIG. 47 the process of closing the clamp arms and securing them in the closed state can be performed simultaneously to uncoupling the control wire 4 from the clamp arms 7a, 7b.

FIG. 54 to FIG. 73 show another embodiment of a medical device according to the present disclosure.

The medical device according to this embodiment includes a handle 1, a sheath device 2, which is attached to the handle 1, and a clamp device 3 which is provided on the distal end of the sheath device 2. A control wire 4 extends through the sheath device 2 and is at its proximal end connected to an actuator 5, which is slidingly held on the handle 1 and can be actuated to reversibly move the control wire 4 in the distal and proximal directions.

The clamp device 3 includes a clamp base 6 formed as a sleeve and two clamp arms 7a, 7b, which are each coupled to the distal end of the control wire 4. Specifically the two clamp arms 7a, 7b are separate elements/components that are coupled to the control wire 4 by means of a pivot pin 8, which is provided at a distal end section of the control wire 4 and extends through corresponding through-holes 9 provided in proximal end sections of the clamp arms 7a, 7b. In the present embodiment the pivot pin 8 is provided on a coupling head 10, which is provided at the distal end of the control wire 4. In this embodiment the coupling head 10 is flat and arranged between the clamp arms 7a, 7b, and the pivot pin 8 has two pivot pin sections 8a, 8b extending from opposite sides of the coupling head 10 to engage the respective through-holes 9 in the clamp arms 7a, 7b.

The two clamp arms 7a, 7b are coupled to the distal end of the control wire 4 so that they can be rotated around a common pivot axis formed by the pivot pin 8 in order to open and close the clamp arms.

Each clamp arm 7a, 7b is provided with a guide groove 11, and the guide grooves 11 of the clamp arms 7a, 7b partially overlap each other. The clamp device 3 further includes a guide pin 12, which is attached to the clamp base 6 and extends through the guide grooves 11 in the overlapping parts thereof, so that by the engagement of the guide pin 12 and the guide grooves 11 a movement of the control wire 4 in the proximal direction is translated into a closing movement of the clamp arms 7a, 7b, and a movement of the control wire 4 in a distal direction is translated into an opening movement of the clamp arms 7a, 7b around the pivot axis.

The through-holes 9 for the pivot pin 8 in the proximal end sections of the clamp arms 7a, 7b are open to their rear (proximal) side. In other words, exit-passages 14 are provided in tail ends of the clamp arms 7a, 7b at the proximal sides of the through-holes 9, through which after closing the clamp arms 7a, 7b the pivot pin 8 can be pulled out of the through-holes 9 spreading apart the tail end sections 15, 16 of the clamp arms 7a, 7b on opposite sides of the openings without breaking. In this way the control wire 4 is uncoupled from the clamp arms 7a, 7b and accordingly the clamp device 3. The exit-passages 14 are here formed by slits in the tail ends of the clamp arms 7a, 7b.

In this embodiment the tail end sections 15, 16 of the clamp arms 7a, 7b are plastically deformed, when they are spread apart, and they are formed as hooks, which engage behind a shoulder 17 of the clamp base 6 in order to lock the clamp arms 7a, 7b therein, as will be described. The shoulder 17 is formed by an annular, inwardly directed projection that is provided at the distal end of the clamp base 6 and forms a distal end surface thereof.

The sheath device 2 includes a coiled sheath 2a, which is connected to the handle 1, and a connect tube 2b, which is provided on a distal end of the coiled sheath 2a and laser welded thereto, so that the sheath device 2 forms an inseparable unit. The sheath device 2 is connected to the clamp base 6 by means of two connecting elements 18 in the form of elastic connecting arms that are formed in a one piece construction with the connect tube 2b on opposite sides thereof. Specifically the proximal ends of the connecting elements 18 are fixedly connected to the connect tube 2b, whereas the free distal ends of the connecting elements 18 form engagement portions that engage a circumferential groove 19 which is provided in an outer surface of the clamp base 6, in order to couple the clamp base 6 to the sheath device 2.

As obtainable from the figure, the proximal end of the clamp base 6 extends into the connect tube 2b.

The connecting elements 18 are provided in the form of resilient, elastically deformable connecting arms or connecting wires, of which a proximal end is attached to the connect tube 2b and a distal end extends out of the connect tube 2b through an opening 23 in the circumferential wall thereof and forms an engagement portion which engages a ring groove 19 provided in the outer circumferential surface of the clamp base 6. Specifically the proximal ends of the connecting elements 18 are fixed to the inner surface of the connect tube 2b, namely inserted into corresponding radial bores in the connect tube 2b. The connecting elements 18 have inwardly bulged sections 18a located in the connect tube 2b, and on the distal side of the bulged section 18a the connecting elements 18 extend out of the connect tube 2b through windows 23 provided in the circumferential wall of the connect tube 2b. (see FIG. 70).

A release arrangement for disconnecting the clamp base 6 from the connect tube 2b is provided. This release arrangement includes a protrusion 20 provided on the control wire 4. The protrusion 20 cooperates with and is located between the inwardly bulged sections 18a of the connecting elements 18 to press the inwardly bulged sections 18a outwardly elastically deforming the connecting element 18 in such a way that their free ends are pressed inwardly into the ring groove 19 of the clamp base 6. When the control wire 4 is pulled proximally and the protrusion 20 comes out of engagement of the connecting elements 18, the bulged sections 18a are re-deformed inwardly by their elastic restoring force to obtain their original shape and the connecting portions come out of engagement of the ring groove 19.

In order to obtain that function provision is made that when in engagement with the protrusion 20 the connecting elements 18 are pushed outwardly, distal sections thereof are pressed against slanted abutment faces 24 on the proximal sides of the windows 23, leading to an inward deformation of the distal ends of the connecting elements 18 so that their connecting portions are pressed into the ring groove 19. When the protrusion 20 comes out of engagement from the connecting elements 18, the later regain their original shape. As a consequence the distal ends of the connecting elements 18 come out of contact from the corresponding abutment faces 24 and are thus deformed to leave the ring groove 19.

In use the clamp device 3 is delivered to a target site through an endoscope, and the clamp device 3 is fixed at a predetermined position on the target site to a blood vessel. In order to pinch the blood vessel the clamp arms 7a, 7b can be repeatedly opened and closed by moving the control wire 4 in the distal and proximal directions by means of the actuator 5.

Once the clamp device 3 has been set the clamp arms 7a, 7b are to be disconnected from the control wire 4. For this purpose the control wire 4 is pulled in the proximal direction in order to fully close the clamp arms 7a, 7b and secure them in the closed position, as depicted in FIG. 17 to FIG. 19. These figures show that the guide grooves 11 have a straight, axially extending distal end section 11a, in which the guide pins 12 can move without incurring further rotation of the clamp arms 7a, 7b. When the guide pins 12 reach their front, distal end positions in the guide grooves 11, they are secured/locked in this position by holding noses 21 provided on the clamp arms 7a, 7b. The holding noses 21 extend into the straight end sections 11a of the guide grooves 11 from a lateral side thereof and are designed in such a way, that the holding noses allow the guide pins 12 to pass them to reach the proximal ends of the guide grooves 11 but prevent passing of the guide pins 12 in an opposite direction. Specifically the holding noses 21 are designed such that the holding noses elastically deform into recesses 11b in lateral sides of the guide grooves 11 when the guide pins 12 press against their proximal side to allow the guide pins 12 to pass the holding noses 21 and reach their distal end positions in the guide grooves 11, that the holding noses regain their initial form by their elastic restoring force to engage behind the guide pins 12, when the guide pins 12 have reached their final positions, but that the holding noses cannot be deformed to open the guide grooves 11 when the guide pins 12 press against their distal sides, so that the guide pins 12 are captured in their distal end positions in the guide grooves 11. In this way the clamp arms 7a, 7b are securely locked to the clamp base 6 and accordingly the clamp housing.

If the control wire 4 is further pulled back, a transitional movement of the clamp arms 7a, 7b is no more possible, and insofar the pivot pin 8 is pulled out of the through-holes 9 through the exit-passages 14 on the rear side thereof. During this process the tail end sections 15, 16 located on the opposite sides of the exit-passages 14 are plastically spread apart to open the exit-passages 14.

In order to uncouple/release the clamp base 6 from the sheath device 2, the control wire 4 is further pulled back in the proximal direction, so that the protrusion 20 of the coupling head 10 comes out of engagement from the inwardly bulged sections 18a of the connecting elements 18, so that the connecting elements 18 regain the initial shape in which their free ends come out of engagement from the ring groove 19 of the clamp base 6.

During the closing process of the clamp arms 7a, 7b, the tail ends of the clamp arms 7a, 7b enter the clamp base 6 through the central opening of the ring shaped shoulder 17, so that the clamp arms engage behind the shoulder 17 of the clamp base 6 in order to lock the clamp arms 7a, 7b to the clamp base 6.

Optionally, as shown in FIG. 11 to FIG. 17, in the medical device provided in various embodiments of the present disclosure, the clamp arms 7a, 7b of the clamp device 3 may be provided thereon with at least two tooth-shaped parts, hereinafter referred to as side teeth, and optionally, each side tooth is integrally formed with the corresponding clamp arms 7a, 7b. In the above, each side tooth has a tooth top and a tooth bottom, and the number of side teeth that each clamp arm has is the same. Optionally, each side tooth of the clamp arm 7a on one side is symmetrical in position and opposite in tooth form to each side tooth of the clamp arm 7b on the other side. For example, as shown in FIG. 11 to FIG. 20 of the present disclosure, at least two side teeth on each clamp arm are distributed on two sides of the clamp arm in an axial direction (namely, a length direction), and have the same positions, and opposite tooth forms. Here, taking the clamp arm 7a on one side as an example, as shown in the figure, the tooth form on a left side of the clamp arm in the axial direction is a male tooth, and the tooth form on a right side is a female tooth. Therefore, inverting the clamp arm 7a on one side 180 degrees around an axis thereof just can obtain the clamp arm 7b on the other side. By adopting such a design, for the clamp arms 7a, 7b of the clamp device 3 provided in the present disclosure, using one kind of mode can manufacture the clamp arms at two sides, thereby simplifying the manufacturing process and reducing the production cost. By providing the above side teeth on each clamp arm, the medical device can more securely grasp biological tissues, thereby making the operation more safely controllable when it is applied to clinical hemostasis and wound surface closure.

INDUSTRIAL APPLICABILITY

The present disclosure provides a medical device for tissue hemostasis or closure that is easy to operate as well as easy to manufacture and assemble. In the medical device of the present disclosure, the clamp arms are directly coupled to the control wire, thus omitting the necessity to provide for a separate connecting element for example in the form of a J-hook, so that the medical device of the present disclosure is easier to manufacture and assemble; and the tail end sections of the clamp arms are elastically or plastically deformed, when they are spread apart. In any way the arrangement is such that the tail end sections do not break in order to avoid, that parts of the breakable arms remain freely in the body of a patient; the clamp arms may be directly locked to the clamp base, without the need for another separate locking element, so that the medical device of the present disclosure is easier to manufacture and assemble; and the clamp base is simple in structure, thus keeping the manufacturing costs low.

What is claimed is:

1. A medical device for tissue hemostasis or closure for use through an endoscope, the medical device comprising:
   a handle;
   a sheath device, which is attached to the handle;
   a clamp device, comprising a clamp base in particular in a form of a sleeve provided on a distal end of the sheath device, and at least or exactly two clamp arms;
   a control wire, extending through the sheath device and reversibly movable in distal and proximal directions; and
   an actuator, coupled to a proximal end of the control wire and actuable to reversibly move the control wire in the distal and proximal directions,
      wherein the clamp arms are each coupled to a distal end of the control wire and wherein the clamp device is actuable to open and close the clamp arms by a movement of the control wire such that a movement of the control wire in the proximal direction is translated into a closing movement of the clamp arms and a movement of the control wire in the distal direction is translated to an opening movement of the clamp arms; and
      wherein the clamp arms are coupled to the control wire by means of a pivot pin which is provided at a distal end section of the control wire and extends through corresponding through-holes provided in proximal end sections of the clamp arms, and exit-passages are provided in tail ends of the clamp arms, through which after closing the clamp arms the pivot pin is able to be pulled out of engagement from the through-holes and from the clamp arms, thereby spreading apart tail end sections of the clamp arms on opposite sides of the exit-passages without breaking them, by a proximal movement of the control wire, in order to uncouple the control wire from the clamp arms.

2. The medical device according to claim 1, wherein the exit-passages are formed by slits in tail ends of the clamp arms.

3. The medical device according to claim 2, wherein the tail end sections of the clamp arms are elastically deformed, when they are spread apart, or proximal ends of the clamp arms are plastically deformed, when they are spread apart.

4. The medical device according to claim 2, wherein a coupling head is provided at a distal end of the control wire, and the pivot pin is provided on the coupling head.

5. The medical device according to claim 1, wherein the tail end sections of the clamp arms are elastically deformed, when they are spread apart, or proximal ends of the clamp arms are plastically deformed, when they are spread apart.

6. The medical device according to claim 5, wherein the tail end sections of the clamp arms on opposite sides of the exit-passages engage behind at least one shoulder of the clamp base in order to lock the clamp arms to the clamp base.

7. The medical device according to claim 6, wherein the tail end sections of the clamp arms on opposite sides of the exit-passages form hooks that engage behind the at least one shoulder of the clamp base in order to lock the clamp arms to the clamp base.

8. The medical device according to claim 7, wherein the shoulder is formed by an annular projection of the clamp base, wherein the annular projection in particular forms a distal end face of the clamp base with a central opening, through which the tail end sections of the clamp arms extend into the clamp base when the clamp arms are fully closed.

9. The medical device according to claim 6, wherein the shoulder is formed by an annular projection of the clamp base, wherein the annular projection in particular forms a distal end face of the clamp base with a central opening, through which the tail end sections of the clamp arms extend into the clamp base when the clamp arms are fully closed.

10. The medical device according to claim 1, wherein a coupling head is provided at a distal end of the control wire, and the pivot pin is provided on the coupling head.

11. The medical device according to claim 10, wherein the pivot pin has two pivot pin sections, extending from opposite sides of the coupling head into the through-holes of the clamp arms which are positioned on the opposite sides of the coupling head.

12. The medical device according to claim 10, wherein the coupling head comprises a U-shaped holding structure open to its distal side, wherein the clamp arms are partly arranged between legs of the U-shaped holding structure and the pivot pin is held between the legs of the U-shaped holding structure and extends through the through-holes of the clamp arms, and wherein, in particular, the clamp arms extend laterally outwards of an open lateral side of the U-shaped holding structure.

13. The medical device according to claim 1, wherein each of the clamp arms is provided with at least two side teeth, wherein at least two side teeth on a clamp arm on one side are distributed on two sides of the clamp arm in an axial direction, and have the same positions and opposite tooth forms.

14. A medical device for tissue hemostasis or closure for use through an endoscope, the medical device comprising:
- a handle;
- a sheath device, which is attached to the handle;
- a clamp device, comprising a clamp base in particular in a form of a sleeve provided on a distal end of the sheath device, and at least or exactly two clamp arms;
- a control wire, extending through the sheath device and reversibly movable in distal and proximal directions; and
- an actuator, coupled to a proximal end of the control wire and actuable to reversibly move the control wire in the distal and proximal directions,
  - wherein the clamp arms are each coupled to a distal end of the control wire and wherein the clamp device is actuable to open and close the clamp arms by a movement of the control wire such that a movement of the control wire in the proximal direction is translated into a closing movement of the clamp arms and a movement of the control wire in the distal direction is translated to an opening movement of the clamp arms, and
- in particular according to claim 1, wherein the clamp device comprises
- exactly two clamp arms, which are provided as separate elements which are coupled to a distal end of the control wire in a pivotal manner around a common pivot axis defined by a pivot pin, wherein each of the clamp arms is provided with a guide groove and guide grooves of the two clamp arms partially overlap each other; and
- a guide pin, which is attached to the clamp base and extends through the guide grooves in an overlapping parts thereof, so that by an engagement of the guide pin and the guide grooves a movement of the control wire in the proximal direction is translated into a closing movement of the clamp arms and a movement of the control wire in the distal direction is translated into an opening movement of the clamp arms around the pivot axis.

15. The medical device according to claim 14, wherein the guide pin is held between two bearing arms extending in the distal direction from the clamp base in particular at free end sections of the bearing arms.

16. The medical device according to claim 14, wherein holding noses are provided on the clamp arms, with the holding noses extending into the guide grooves from a lateral side thereof and being designed in such a way, that they allow the guide pins to pass them to reach distal ends of the guide grooves but prevent passing of the guide pins in an opposite direction, wherein, in particular, the guide grooves have a straight, axially extending distal end section, in which the guide pins is able to move without incurring rotation of the clamp arms and the holding noses extend into the straight distal end sections.

17. The medical device according to claim 16, wherein recesses are formed in lateral sides of the guide grooves on a distal side of the holding nose, into which the holding noses are elastically deformed to allow the guide pins to pass the holding noses and reach their distal end positions in the guide grooves.

18. The medical device according to claim 14, wherein each of the clamp arms is provided with at least two side teeth, wherein at least two side teeth on a clamp arm on one side are distributed on two sides of the clamp arm in an axial direction, and have the same positions and opposite tooth forms.

* * * * *